US012788671B2

(12) United States Patent
Yarro et al.

(10) Patent No.: US 12,788,671 B2
(45) Date of Patent: Nov. 10, 2026

(54) AUTOMATED SKELETAL MUSCULATURE, JOINT, FACIA AND SKIN THERAPY SYSTEM AND METHODS OF USE

(71) Applicant: Madman X, LLC, Cheyenne, WY (US)

(72) Inventors: Justin C. Yarro, Orem, UT (US); Michael J. Brooking, Orem, UT (US)

(73) Assignee: Madman X, LLC, Cheyenne, WY (US)

(*) Notice: Subject to any disclaimer, the term of this patent is extended or adjusted under 35 U.S.C. 154(b) by 781 days.

(21) Appl. No.: 18/349,133

(22) Filed: Jul. 8, 2023

(65) Prior Publication Data

US 2024/0009070 A1 Jan. 11, 2024

Related U.S. Application Data

(60) Provisional application No. 63/359,975, filed on Jul. 11, 2022.

(51) Int. Cl.

| | |
|---|---|
| ***A61H 15/00*** | (2006.01) |
| ***A61H 15/02*** | (2006.01) |
| ***A61N 5/00*** | (2006.01) |
| ***A61N 5/06*** | (2006.01) |

(52) U.S. Cl.

CPC ......... *A61H 15/0078* (2013.01); *A61H 15/02* (2013.01); *A61N 5/0616* (2013.01); *A61H 2015/0028* (2013.01); *A61H 2201/0103* (2013.01); *A61H 2201/0107* (2013.01); *A61H 2201/10* (2013.01); *A61H 2201/1654* (2013.01); *A61H 2201/1669* (2013.01); *A61H 2201/5035* (2013.01); *A61N 2005/005* (2013.01); *A61N 2005/0652* (2013.01); *A61N 2005/0659* (2013.01)

(58) Field of Classification Search

CPC ........ A61H 15/0078; A61H 2015/0028; A61H 2201/0103; A61H 2201/1654; A61H 2201/1669; A61H 7/007; A61N 5/0616

See application file for complete search history.

(56) References Cited

U.S. PATENT DOCUMENTS

| | | | | |
|---|---|---|---|---|
| 1,899,208 A * | 2/1933 | Murphy | A61H 15/0085 | 601/113 |
| 5,137,016 A * | 8/1992 | Yamasaki | A61H 15/0078 | 601/102 |
| 6,432,072 B1 | 8/2002 | Harris et al. | | |

(Continued)

FOREIGN PATENT DOCUMENTS

| | | | | |
|---|---|---|---|---|
| CN | 101778612 | | 10/2013 | |
| CN | 108245405 A | * | 7/2018 | A61H 39/04 |
| KR | 20160046011 | | 4/2016 | |

OTHER PUBLICATIONS

Translation of Zhao et al. (CN-108245405-A) (Year: 2018).*

(Continued)

*Primary Examiner* — Valerie L Woodward

(57) ABSTRACT

A system for automated massage therapy that may include a vessel and a dome that create a cavity that may be pressurized, and the cavity includes motorized rotary sprocket, where the sprocket may include one or more wheels for providing peristaltic wave massage therapy. The system may be mounted on a rail that is mounted on a wall. The system may be controlled remotely or directly.

20 Claims, 30 Drawing Sheets

(56) References Cited

U.S. PATENT DOCUMENTS

| | | | | |
|---|---|---|---|---|
| 10,034,814 | B2 | 7/2018 | Zhang | |
| 11,103,673 | B2 | 8/2021 | Bae et al. | |
| 11,648,173 | B2 | 5/2023 | Gagliano et al. | |
| 2005/0143679 | A1 | 6/2005 | Gelber et al. | |
| 2009/0076421 | A1 | 3/2009 | Grant, Jr. | |
| 2010/0191160 | A1 | 7/2010 | Avramovich et al. | |
| 2011/0055720 | A1 | 3/2011 | Potter et al. | |
| 2012/0179074 | A1 | 7/2012 | Ikebe et al. | |
| 2013/0012851 | A1 | 1/2013 | Fahmie | |
| 2014/0005580 | A1* | 1/2014 | Brueggemann .... | A61H 15/0078 601/118 |
| 2016/0113837 | A1 | 4/2016 | Burson | |
| 2019/0167512 | A1 | 6/2019 | Forsythe et al. | |
| 2022/0104997 | A1 | 4/2022 | Lawrie | |

OTHER PUBLICATIONS

Mynta Newly Upgraded 3D Massage Chair https://www.amazon.com/Real-Relax-Warranty-Approved-Affordable/dp/B06W2GYD8Y/ref=sr_1_15?geniuslink=true&keywords=Luraco%2BiRobotics%2B7%2BPLUS%2BMassage%2BChair&qid=1689110543&sr=8-15&ufe=app_do%3Aamzn1.fos.2b70bf2b-6730-4ccf-ab97-eb60747b8daf&th=1 Sep. 25, 2023.

Roll Shaper by STUDIOfigura https://rollshaper.com/ Sep. 25, 2023.

Thriftyfun Finding Vintage Roller Exercise Machine https://www.thriftyfun.com/Finding-a-Vintage-Roller-Exercise-Machine.html Sep. 25, 2023.

Therabody Theragun https://www.therabody.com/us/en-us/massage-guns/?utm_a=1331510299613137&msclkid=36c2202afc731cbd8987448739df6031&utm_source=bing&utm_medium=cpc&utm_campaign=Search_Bing_Perf_BR-Text_Exact_Conv_X_US_ENG_Theragun&utm_term=Theragun&utm_content=Search_Bing_Perf_BR-ext_Exact_Conv_X_US_ENG_Theragun_Theragun_X_X_X_X Sep. 25, 2023.

AcuRelax Massage Beds http://www.acurelax.com/products/massage-beds Sep. 25, 2023.

Jade Roller Bed https://www.bing.com/images/search?view=detailV2&ccid=G0Nr7cYx&id=54BD3AA8F316C43D9DA20B8813524AE4B908F05F&thid=OIP.G0Nr7cYxT0c_lz8SsXYhWQHaGI&mediaurl=https%3a%2f%2fsc02.alicdn.com%2fkf%2fHTB18sX2laAoBKNjSZSyq6yHAVXaO%2f200164771%2fHTB18sX2laAoBKNjSZSyq6yHAVXaO.jpg&cdnurl=https%3a%2f%2fth.bing.com%2fth%2fid%2fR.1b436bedc6314f473f973f12b1762159%3frik%3dX%252fAIueRKUhOICw%26pid%3dlmgRaw%26r%3d0&exph=621&expw=750&q=jade+roller+bed&simid=607999492250675370&FORM=IRPRST&ck=19C51021B4D54FE0A9245447BEC7E162&selectedIndex=11&ajaxhist=0&ajaxserp=0 Sep. 25, 2023.

AliExpress Physical Infrared Reflexology Foot Massager Electric Machine Automatic Roller Feet Care Massager Circulation Therapy SPA https://www.aliexpress.us/item/2251832780668519.html?gatewayAdapt=glo2usa4itemAdapt Sep. 25, 2023.

* cited by examiner

AUTOMATED SKELETAL MUSCULATURE, JOINT, FACIA AND SKIN THERAPY SYSTEM AND METHODS OF USE

1. RELATED APPLICATIONS

This utility patent application claims the benefit of U.S. Provisional Patent Application Ser. No. 63/359,975 filed on Jul. 11, 2022, which is hereby incorporated by reference in its entirety.

BACKGROUND

1. Field of the Invention

This invention relates to a system for automated skeletal musculature, joint, facia, and skin therapy, more particularly, a device that can provide various musculature therapies to a wide range of body parts and areas in home, office, or similar setting. The massage device may include a core mounted on a rail or track. The rail may be mounted to a wall, ceiling or other suitable foundation. The core may provide a variety of massage and musculature therapies to a user.

2. The Background Art

Massage and physical therapy have been used to promote health and healing for centuries. There are multiple types of massage therapies. One common form is Swedish or classical massage. Other types of massage may be described as sports massage and clinical massage. Massage traditions from Eastern cultures include Shiatsu, Guasha and Tuina. Guasha, also known as scraping or tribo-effleurage, is an intense peristaltic type therapy that has been shown to help heal muscles and joints, and is part of current western physical therapy post-injury, post-surgery, and for chronic injuries and pain alleviation.

In massage therapy and physical therapy, a massage therapist may rub, knead, and/or scrape the soft tissues a person's body, including without limitation, muscles, tendons, ligaments, connective tissue, skin, and the like. The massage therapist may vary the movement and the amount of pressure applied. Studies of massage therapy and/or physical therapy have found that the benefits of massage may include a reduction of stress, a decrease in muscle pain and tightness, an increase in relaxation, facilitation of the healing process, an increase in strength, an increase in range of motion, and an improvement in the function of the immune system.

While there are certainly benefits to physical therapy and massage therapy, one drawback is that a massage therapist, or a therapist, may begin to tire during a prolonged session of massage therapy, which can result in a decrease in the quality and effectiveness of the massage. It would be an improvement in the art to provide a machine or system that can produce, replicate, or even surpass various types of massage and muscular therapy techniques for an extended period of time, in a repeatable and sustainable fashion. The peristaltic wave therapy is more effective and mimics hand done massage or scraping therapy, as opposed to reciprocal punching type or vibration type therapy. The user would be in control of the pressure both from their own body force against the system or machine and the bubble pressure settings on the system or machine. The user would also be able to retract and protract their muscular systems while engaging the therapy area of the system or machine.

SUMMARY OF THE INVENTION

In one embodiment, an automated massage therapy system may be comprised of three sub-systems, a core, a rail, and a controller. The core primarily provides the means for peristaltic massaging the soft tissues of a person. The rail provides the means for supporting and positioning the system. The controller provides the means for controlling the functions of the core.

A core may provide various means for peristaltic therapy and massaging the soft tissues of a person. For example, and without limitation, a core may include wheels that act to massage muscles and similar tissue using peristaltic waves to increase blood flow and apply gentle or intense pressure to the muscles. A core may include a cavity that may be pressurized at a desired level, thus allowing for varied pressure to be applied by the wheels. The higher the cavity pressure, the shallower the therapy. Conversely, the lower the cavity pressure, the deeper the therapy. A core may provide or simulate various types of massage or muscular therapy techniques.

A rail or track system may be wall mounted. Such a system may be mounted to any suitable surface. A rail system may provide the means for supporting, anchoring, and positioning the core of the system. The core may be integrally, operably connected to the rail or track in a manner that allows the core to move along the track and be locked into place at various points along the track.

A controller may provide means for controlling the therapy or massaging functions of the core. A controller may be programmed to control and vary the therapy or massage functions of the core. This may be done by controlling the speed and pressure of the wheels, the air pressure of a cavity in the core, the direction and configuration of the wheels, and similar features. The controller itself may be of any suitable configuration, and may include a trigger for activating the functions of the core and/or a touch-screen that enables a user to control various massage functions of a core.

In one embodiment, a massage therapy device may be comprised of a track, wherein the track may be comprised of grooves that enable an operable connection between the track and a core, the core may comprise a hub motor and wheels and a bubble, wherein the bubble encloses a cavity that may be pressurized with air, and a controller that controls the various functions of the core.

In one embodiment, a massage therapy apparatus may comprise a vessel, a hub motor operably connected to and within the vessel, wherein the hub motor further comprises a sprocket and a plurality of wheels and the sprocket is operably and rotatably connected to the hub motor and the plurality of wheels is operably and rotatably connected to the sprocket, and the hub motor can rotate the sprocket, and a flexible dome connected to the vessel in a manner that encloses the hub motor, sprocket, and plurality of wheels within a cavity formed by the vessel and the dome, and a bezel removably connected to the vessel, with the dome between the bezel and the vessel, in a manner that seals the cavity, and a controller for controlling the functions of the hub motor. There are two main reasons for this pressurized cavity and flexible dome system. One is to control the depth of the therapy by the rotary wheel. The rotary wheel pushes against the flexible dome, transferring the peristaltic wave therapy to the user. The second reason is for safety, to completely separate the hub motor, sprocket and wheels, or rotary wheel, from the outside world. Thus, there is no possible way for the user to become entangled with the rotary wheel.

In one embodiment, a massage therapy apparatus may further comprise a rail mounted to a wall and a carrier that is operably and rotatably connected to the vessel and the carrier is operably connected to the rail in a manner that allows the carrier and the vessel to move along the rail. The rail may further comprise a power reel at one end and a weight reel at the opposing end. The carrier and the vessel may be operably positionable along the rail. The apparatus may further comprise a pump and a valve both operably disposed within the vessel in a manner that enables pressurization and depressurization of the cavity, which pressurization may be controllable by the controller. The apparatus may further comprise a light array operably connected to the bezel, wherein the lighting array comprises a light source, a heat sink surrounding the light source, and a lens covering the light source. Each of the light sources may be an LED-infrared light source providing infrared light.

In another embodiment, a massage therapy apparatus may further comprise a rail mounted to a wall and a carrier that is operably and rotatably connected to the vessel and the carrier is operably connected to the rail in a manner that allows the carrier and the vessel to move along the rail. The rail may further comprise a power reel and a weight reel at one end of the rail. The carrier and the vessel may be operably positionable along the rail. The apparatus may further comprise a pump and a valve both operably disposed within the vessel in a manner that enables pressurization and depressurization of the cavity, which pressurization may be controllable by the controller. The apparatus may further comprise a light array operably connected to the bezel, wherein the lighting array comprises a light source, a heat sink surrounding the light source, and a lens covering the light source. Each of the light sources may be an LED-infrared light source providing infrared light.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE ILLUSTRATED EMBODIMENTS

Figure 1:
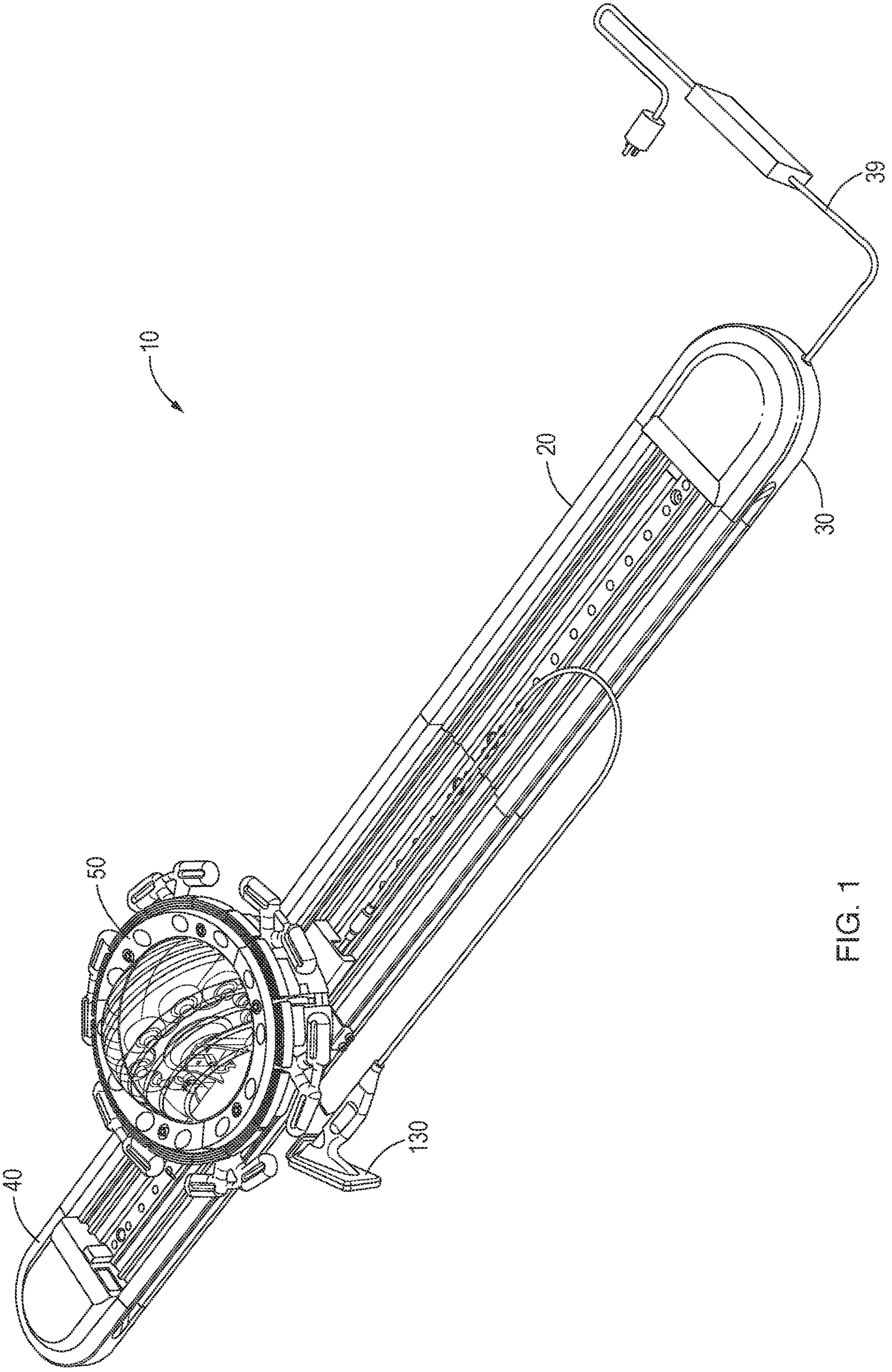
FIG. 1 is a perspective view of an automated musculature therapy system.

It will be readily understood that the components of the present invention, as generally described herein, could be arranged and designed in a wide variety of different configurations. Thus, the following more detailed description of the embodiments of the system, products and methods of use of the present invention, are not intended to limit the scope of the invention, as claimed, but is merely representative of various embodiments of the invention Referring to FIG. 1, the invention relates to an automated system for massage therapy 10. The system 10 may be described as comprising a rail 20 or track 20, a core 50, and a controller 130. The rail 20 will generally have two opposite ends. One end, i.e., a proximate end, may be described as a base 30, or a rail base 30, wherein the base 30 may be disposed at the bottom of the rail 20 when the rail 20 is placed in a vertical direction. However, the rail 20 may also be placed in a horizontal direction, depending on the intended use. Regardless, the rail 20 or track 20 may have a base 30 at one end and a head 40, or rail head 40, at the opposing end. The base 30 may have a power cord 39, or power source 39, operably connected to provide power to the system 10. The controller 130 may be detachably connected to the core 50 and operably connected to the core 50 via a controller cord 138 or string 138.

Figure 2:
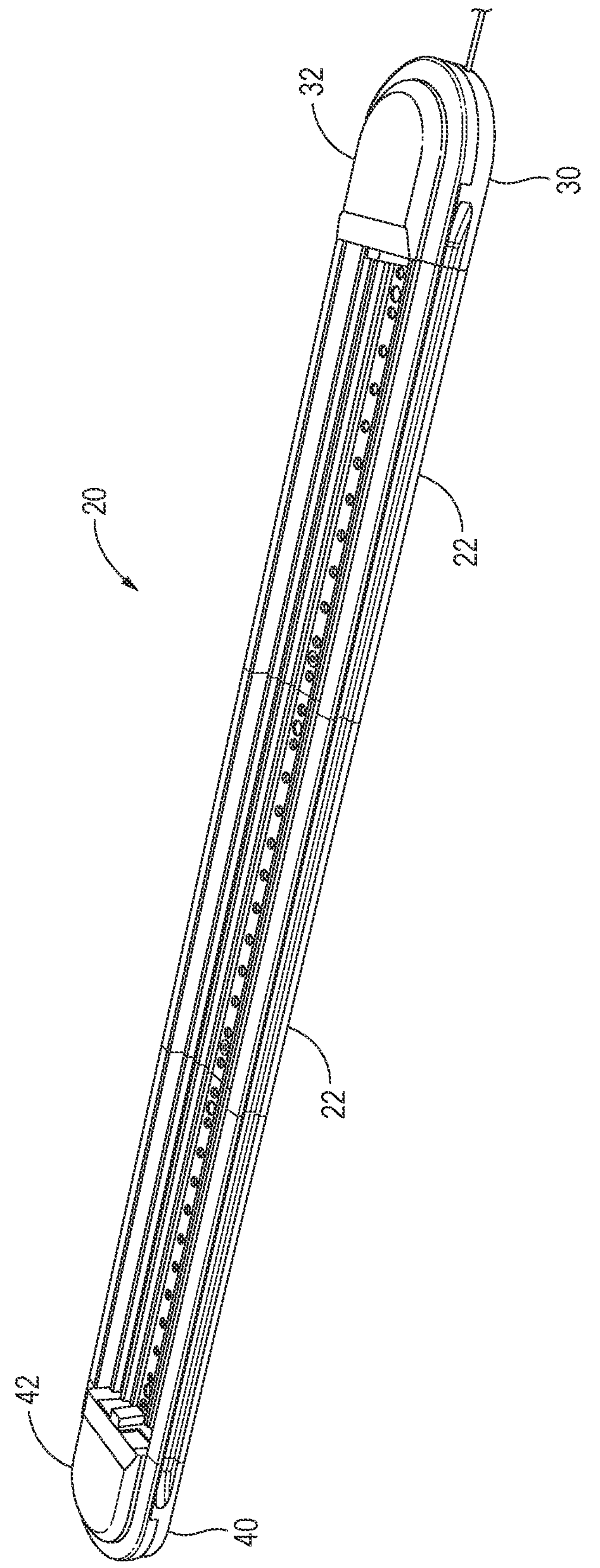
FIG. 2 is a perspective view of a rail or track system.

Referring to FIG. 2, a rail system 20 or track 20 may be comprised of multiple component parts. The rail 20 itself may be comprised of multiple rail segments 22 or track segments 22. The rail 20 will generally have two opposing ends. One end may be described as a proximal end, or rail base 30 or foot 30. The other end may be described as a distal end, or rail head 40. The rail base 30 may include a base cover 32, which base cover 32 can conceal and cover component parts within the rail base 30. Similarly, the rail head 40, or head 40, may include a head cover 42, which head cover 42 can conceal and cover component parts within the rail head 40. A rail system 20 may be mounted to a wall surface in a generally vertical alignment. A rail system 20 may be mounted to a wall surface in a generally horizontal alignment. A rail system 20 may be mounted in any suitable fashion. A rail system 20 may be suspended via a ceiling mount in a manner that allows a system 10 to be utilized from above a user.

Figure 3:
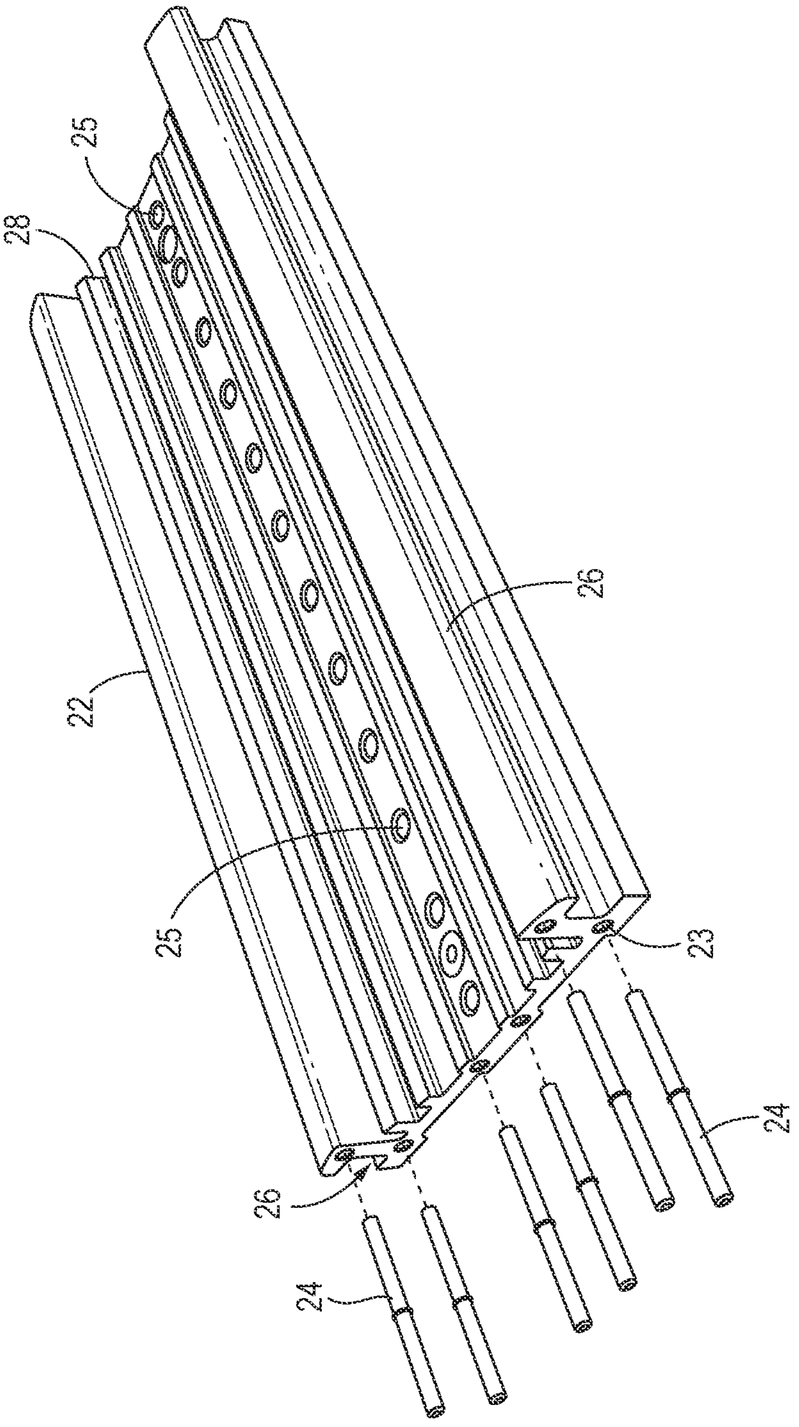
FIG. 3 is a perspective view of a rail segment and exploded view of connector pins for the rail segment.

Referring to FIG. 3, a rail segment 22, or track segment 22, is shown with constituent structures. Multiple rail segments 22 may be joined together using connector pins 24, or pins 24, that may be inserted into connection apertures 23 that align the respective rail segments 22 when connected. Any suitable connection means may be utilized.

A rail segment 22 may comprise multiple position apertures 25. Position apertures 25 may be of any suitable size and shape. Position apertures 25 may be generally arranged down the middle of a rail segment 22 in a linear fashion. The position apertures 25 provide a space where a positioning stem 59 may be inserted so the core 50 may be positioned at varying points along the rail segment 22.

A rail segment 22 may comprise rail grooves 26, or track grooves 26 or grooves 26, where groove wheels 54 may be engaged in a manner that allows the core 50 to move along each rail segment 22 of a rail 20. Any suitable means for moving or sliding the core 50 along the rail 20 may be utilized. A rail segment 22 may comprise a guide 28 or guides 28 that may be formed to allow cables and/or cords to be aligned with the rail 20 in a manner that allows the core 50 to move along the rail 20 without damaging cables and/or cords that may be positioned or attached in guides 28.

Figure 4:
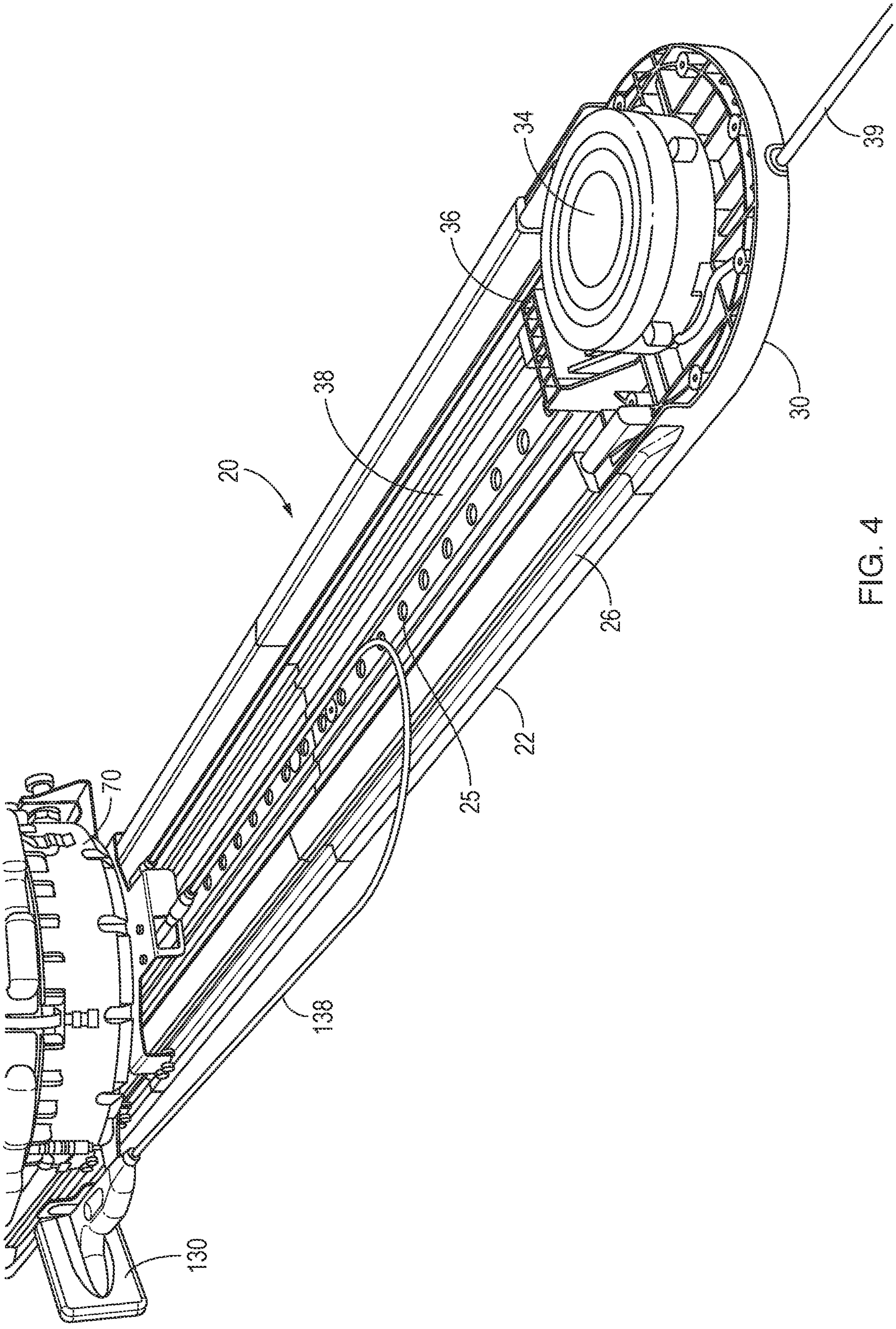
FIG. 4 is a perspective view of one end, a proximal end, of a rail with internal structures.

Referring to FIG. 4, a rail 20 may comprise one end that may be described as a track base 30, or base 30 or foot 30, which may also be described as a proximate end 30 of the rail 20. A track base 30 may comprise a base cover 32 that covers and conceals internal structures. For example, a power reel 34, or base pulley 34, may be positioned in the track base and be operably connected to enable movement of a cable 38. When a cable 38 is connected to a carrier 52, the power reel 34 may operate to move the carrier 52 and core 50 along the rail A track base 30 may comprise a base stop 36 to make sure that a carrier 52 and/or core vessel 70 does not come into contact with the power reel 34 during operation of the system 10. A rail base 30 may also comprise a power cord 39 that is operably connected to the system 10 to provide electrical power to the various components and component parts of the system 10, including without limitation, the core 50, the controller 130, and the power reel 34. A power reel 34 may include the power cord 39, or main power cable 39, which power reel 34 may reel in and reel out the cable depending on the position of the core 50 along the rail 20.

Figure 5:
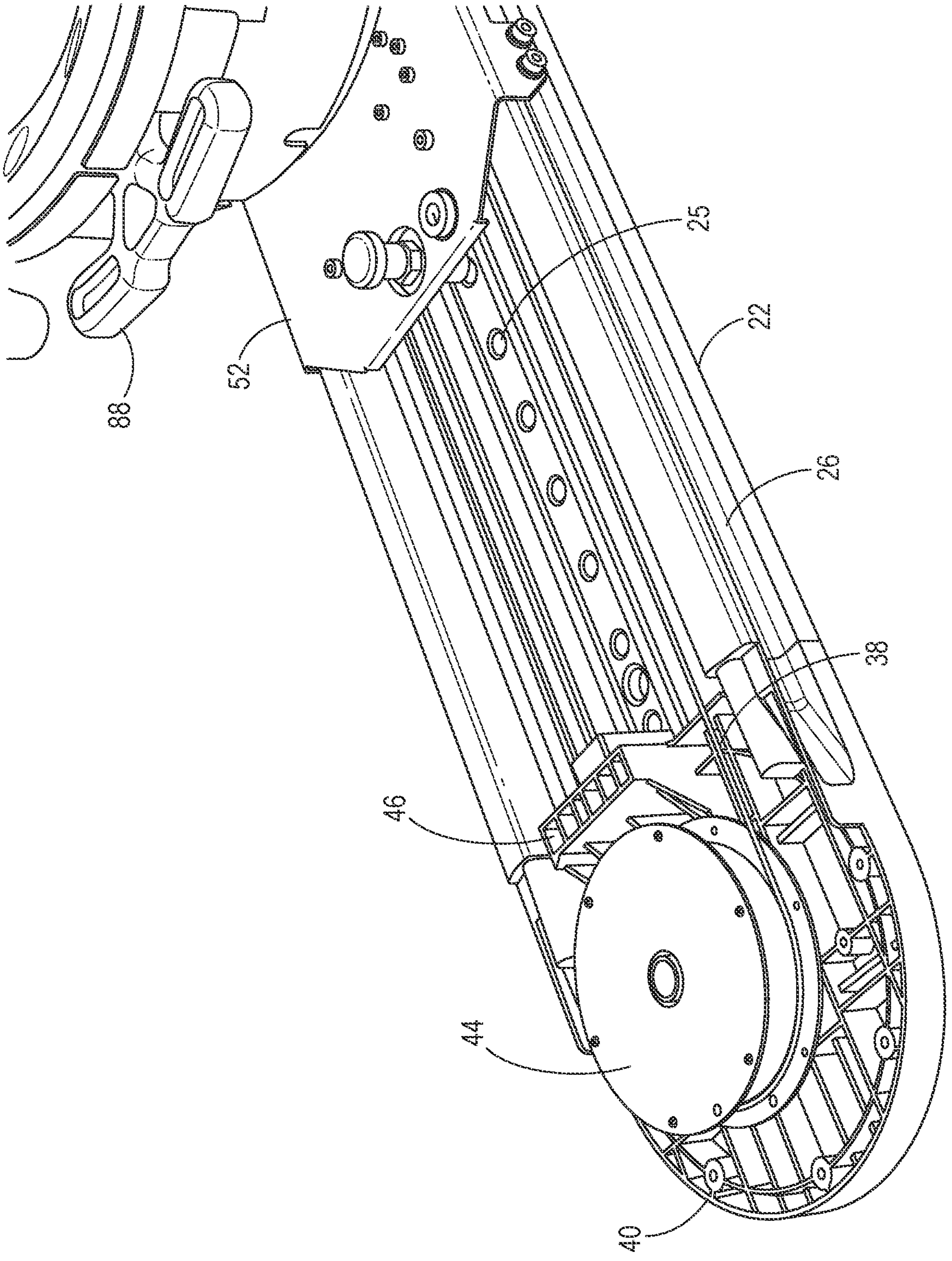
FIG. 5 is a perspective view of one end, a distal end, of a rail with internal structures.

Referring to FIG. 5, a rail 20 may comprise one end that may be described as a rail head 40, or head 40 or track head 40, which may also be described as a distal end 40 of the rail A rail head 40 may comprise a head cover 42 that covers and conceals internal structures. For example, a weight reel 44, or weight pulley 44, may be positioned in the rail head 40 and be operably connected to enable movement and/or anchoring of a cable 38. A rail head 40 may comprise a head stop 46 to make sure that a carrier 52 and/or core vessel 70 does not come into contact with the weight reel 44 during operation of the system 10. A weight reel 44 may include a cable 38 that is connected to a carrier 52 and may counterbalance the weight of the core 50, so that a user can more easily move the core 50 along the rail 20.

Figure 6:
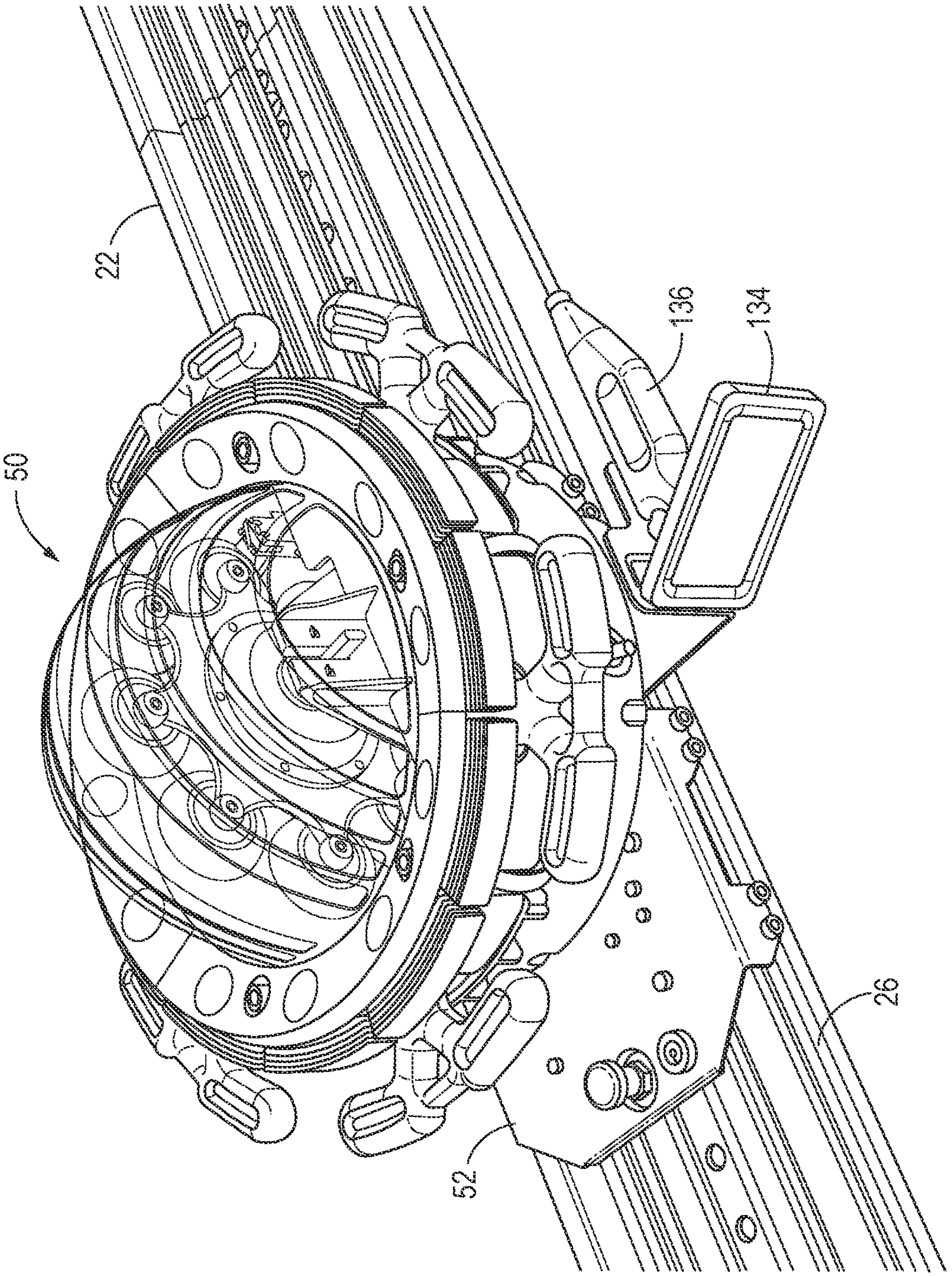
FIG. 6 is a perspective view of a core integrally connected to a rail.

Referring to FIG. 6, a core 50 may be operably connected to a rail 20 or rail segment 22. A core 50 may be integrated with a carrier 52 to enable an operable connection between the core 50 and the rail 20. The carrier 52 may be configured to allow the carrier 52 and core 50 to engage the grooves 26 in a manner that allows the carrier 52 and core 50 to move along the rail 20. With the rail 20 and core 50 mounted to a wall, a user may receive massage therapy on muscles and for body areas that may not be reached with a device operated by hand. For example, a user could position the core 50 so that the user can lean back against the dome 82 to massage back muscles. Also, the amount of pressure applied by the user to the dome 82 can be varied. A core 50 may be operated by hand, without a rail 20, and most likely without a carrier 52. A core 50 may simply be laid on a floor and provide massage therapy from that placement.

Figure 7:
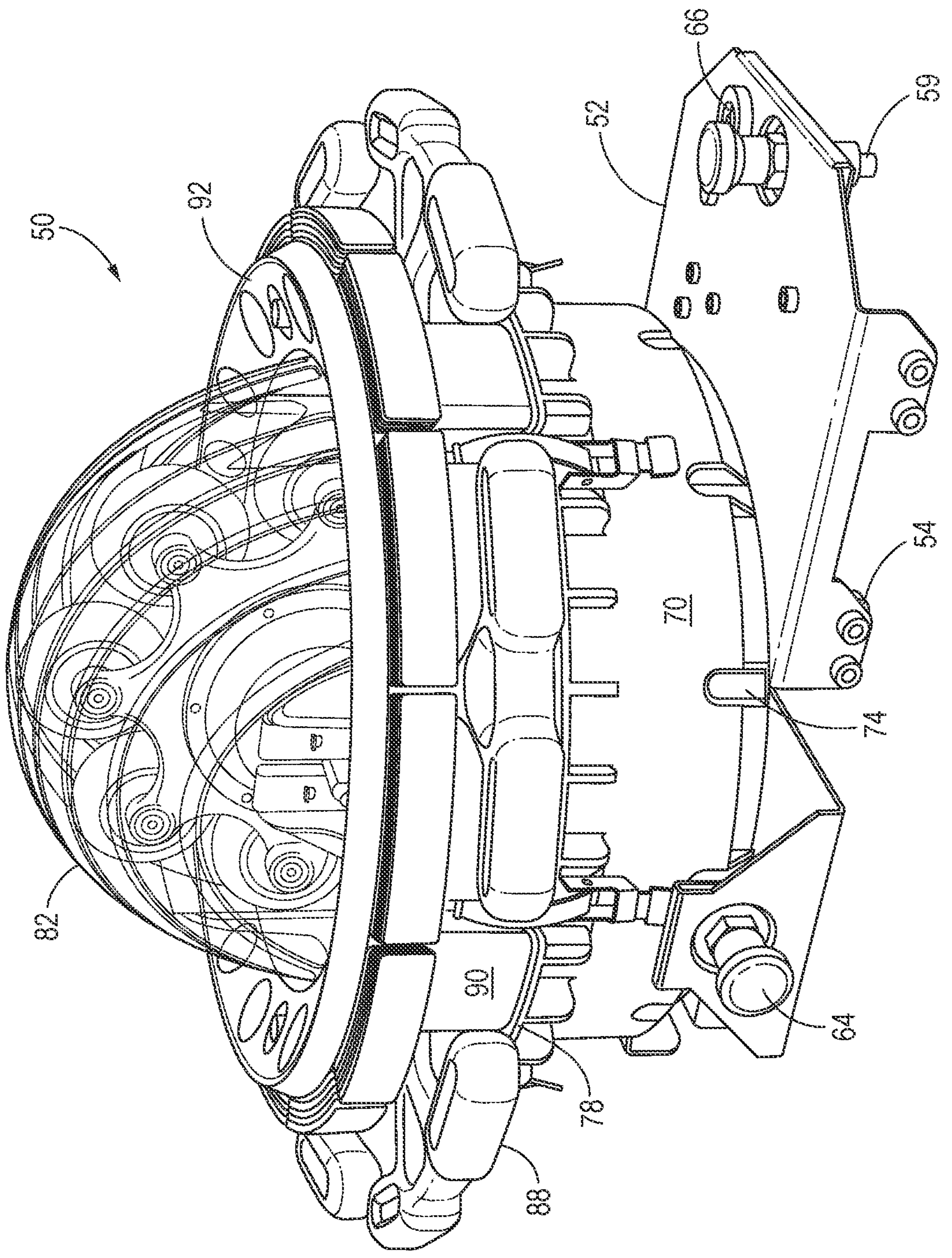
FIG. 7 is a frontal, perspective view of a core.

Referring to FIG. 7, and generally FIGS. 7-20, a core 50 may be comprised of multiple component structures that form the core 50. The core 50 may include a carrier 52, which carrier 52 forms the foundation of the core 50. The core 50 may include a core vessel 70, or vessel 70 or bowl 70, which vessel 70 provides a means for containing multiple component structures related to the core 50. The core 50 may include a dome 82, or bubble 82, which dome 82 provides a protective cover, and means to seal the cavity within for pressurization, for component parts of the core 50, including the hub motor 100, and forms a cavity within the core 50. The cavity is generally defined by the vessel 70 and the dome 82, and may be described as the space enclosed by the vessel 70 and the dome 82. The cavity may include structures like the hub motor 100. The core 50 may include a bezel 90, which bezel 90 provides a mean for securing the dome 82 between the vessel 70 and the bezel 90.

Figure 8:
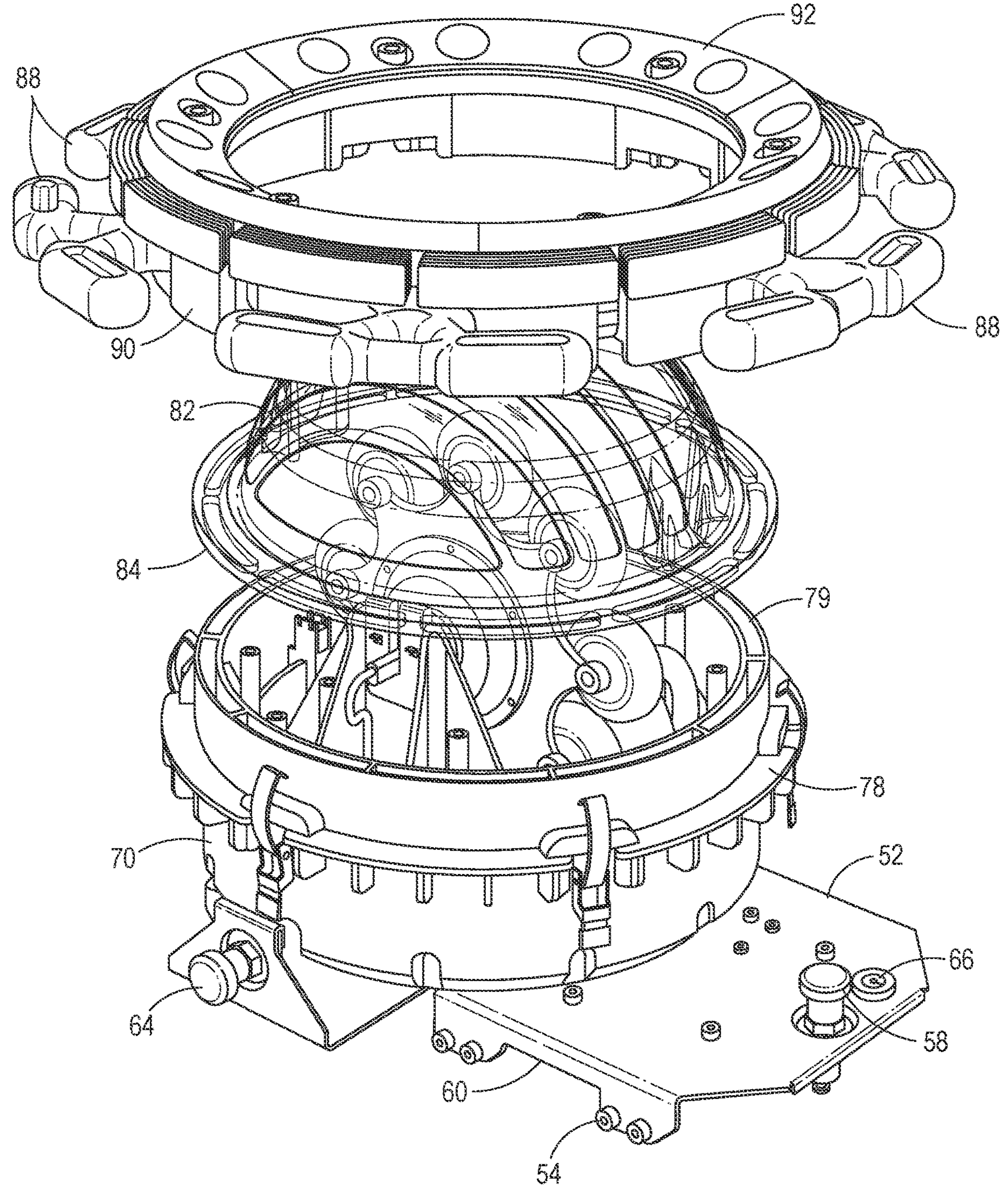
FIG. 8 is an exploded view of a core.

Referring more particularly to FIG. 8, a core 50 may be arranged so that a carrier 52 forms the foundation of the core 50. A vessel 70, or core vessel 70 or bowl 70, may be operably connected to the carrier. A dome 82, or bubble 82, may fit onto the vessel 70, wherein a dome rim 84, or bubble rim 84, rests on a vessel rim 78. A bezel 90 may be placed over the dome 82 and rest on the dome rim 84. Then, a vessel latch 80 may engage a bezel connection 81 in a manner that allows the vessel latch 80 to secure the dome rim 84 between the vessel rim 78 and the bezel 90. Thus, a cavity is formed by the vessel 70, or bowl 70, and the dome 82. This cavity may be air tight so that the cavity can be pressurized and/or depressurized. Also, the vessel latches 80 allow the dome 82 to be removable and/or replaceable, thereby also allowing access to component parts of the core 50 that may be in the cavity.

Figure 9:
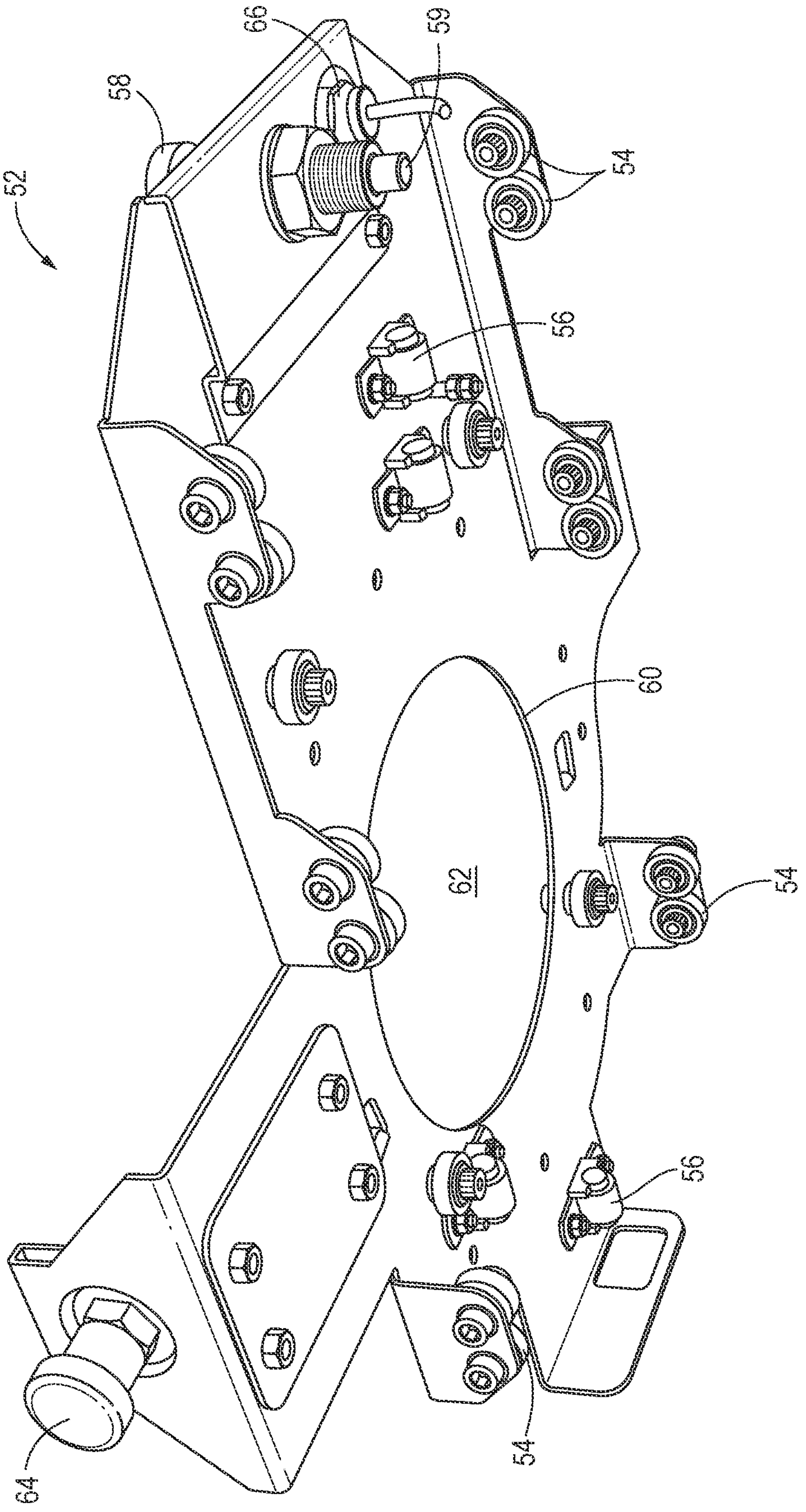
FIG. 9 is an upwards, perspective view of a carrier of a core.

Referring more particularly to FIG. 9, a carrier 52 may be comprised of multiple component parts and structures. A carrier 52 may be comprised of any suitable material, i.e., steel, aluminum or the like. Generally, a suitable material will be strong and somewhat rigid to support other structures. A carrier 52 may include groove wheels 54, or roller bearings 54, which groove wheels 54 may engage grooves

26 on a rail 20 in a manner that allows the carrier 52 to smoothly move along the rail 20. A carrier 52 may be designed to easily slide and/or roll up and down a rail 20 to accommodate any desired level or position along the rail 20. A carrier 52 may include a mount for a controller 130. A carrier 52 may include stop pulls 56, or cable mounts 56, which stop pulls 56 may serve as connection points for cables 38 or other structures. A carrier 52 may include a positioning knob 58 with a positioning stem 59. In one embodiment, a positioning knob 58 may be pulled upwards to retract the positioning stem 59. The positioning knob 58 may then be lowered to insert the positioning stem 59 into a position aperture 25. This may allow for positioning and securing the carrier 52 and core 50 at various points along a rail Thus, the core 50 may be positioned at various heights along a rail 20, or at various lengths along a rail 20.

A carrier 52 may include a table 60, which table 60 may serve as a flat surface or foundation for other component parts. A carrier 52 may include a power switch 66, which power switch 66 may serve as an on/off switch controlling the availability of electrical power to the system 10. The carrier 52 may also include a table aperture 62, which table aperture 62 may serve as a means for cords or other structures to access the core 50 via the vessel 70. A carrier 52 may include a rotation knob 64. In one embodiment, a rotation knob 64 may be pulled upwards to retract a rotation stem. The rotation knob 64 may then be lowered to insert the rotation stem into a rotation aperture 74. This may allow for positioning and securing the core at various rotation points as the core 50 rotates in relation to the carrier 52.

Figure 10:
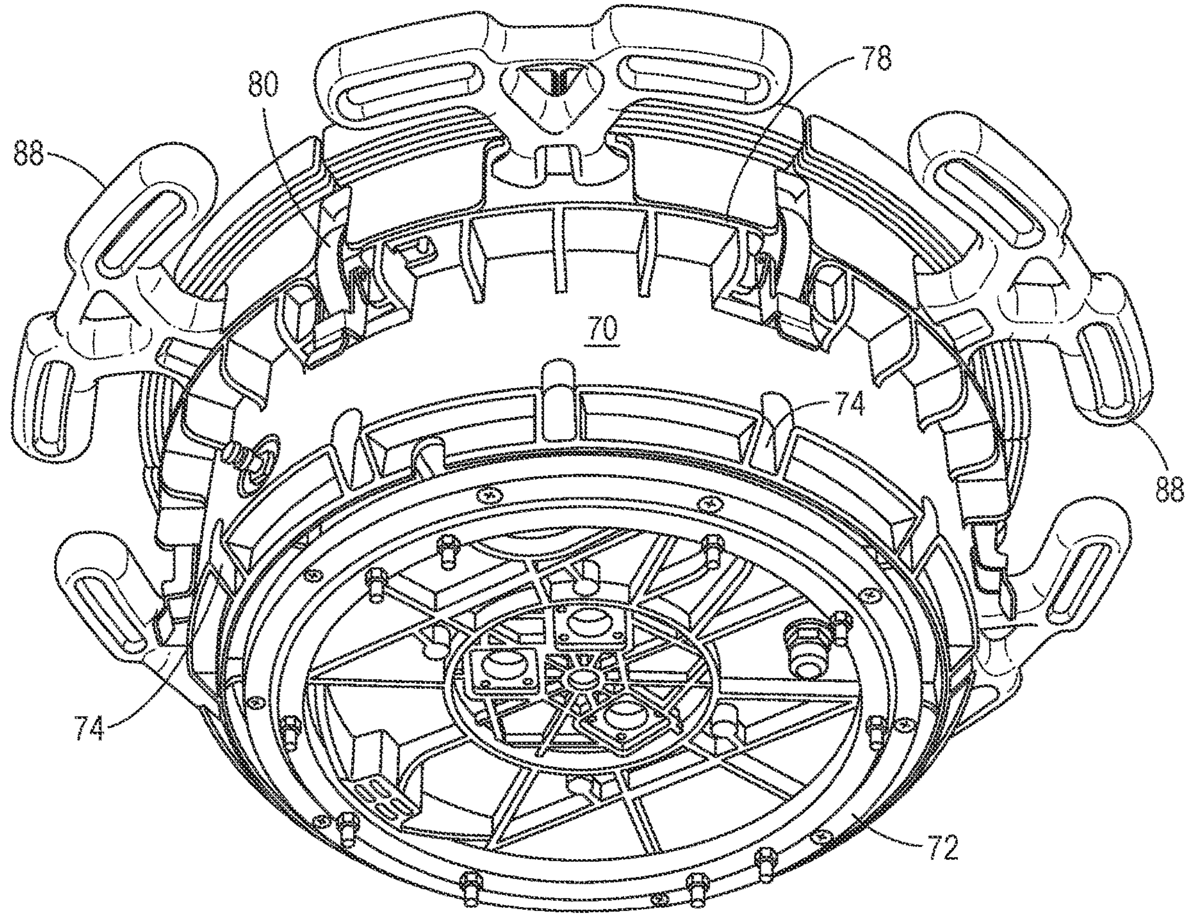
FIG. 10 is an upwards, perspective view of a vessel or bowl of a core.

Referring more particularly to FIG. 10, a vessel 70, or bowl 70, may include various structures and configurations. A vessel 70 may be comprised of any suitable material, i.e., plastic, polymer or the like. Generally, a suitable material will be strong and somewhat rigid to support and contain other structures. A vessel 70 may include a table bearing 72, which table bearing 72 may allow the vessel 70 to be connected to the carrier 52 in a manner that allows the vessel 70 to rotate in relation to the carrier 52. A vessel 70 may be mounted to a table bearing 72 in a manner that allows rotation of the core 50 of 180 degrees or 90 degrees in either direction. The allows the wheels 112 to act on a user's soft tissues, or muscles, in parallel to tissue alignment, or perpendicularly to tissue alignment, or other degrees that are available and/or desirable. A user may select a desired angle to alignment between tissues and a wheeled sprocket.

A vessel 70 may include a vessel bottom 76, or vessel floor 76, that may be positioned substantially over a table aperture 62 when the vessel 70 is rotatably connected to the carrier 52. A vessel 70 may include rotation apertures 74, which rotation apertures 74 may be described as indentations that provide position points for securing the vessel 70 at varied rotations or rotational positions with respect to the carrier. A vessel 70 may include a vessel rim 78, which vessel rim 78 may serve as an engagement surface for a dome rim 84 of a dome 82. A vessel 70 may include a vessel top 79, which vessel top 79 may define the top of the vessel 70 and serve as support for the bottom portion of a dome 82.

A vessel 70 may include two or more vessel latches 80. A vessel latch 80 serves to connect and secure the bezel 90 and the vessel 70. The connection may be releasable so that component parts within the vessel 70 may be accessible, replaced and/or serviced. Also, the connection may be done in a manner that secures the dome rim 84 between the vessel rim 78 and the bezel 90. Again, the connection may be releasable so that the dome 82 may be accessible, replaced and/or serviced.

Figure 11:
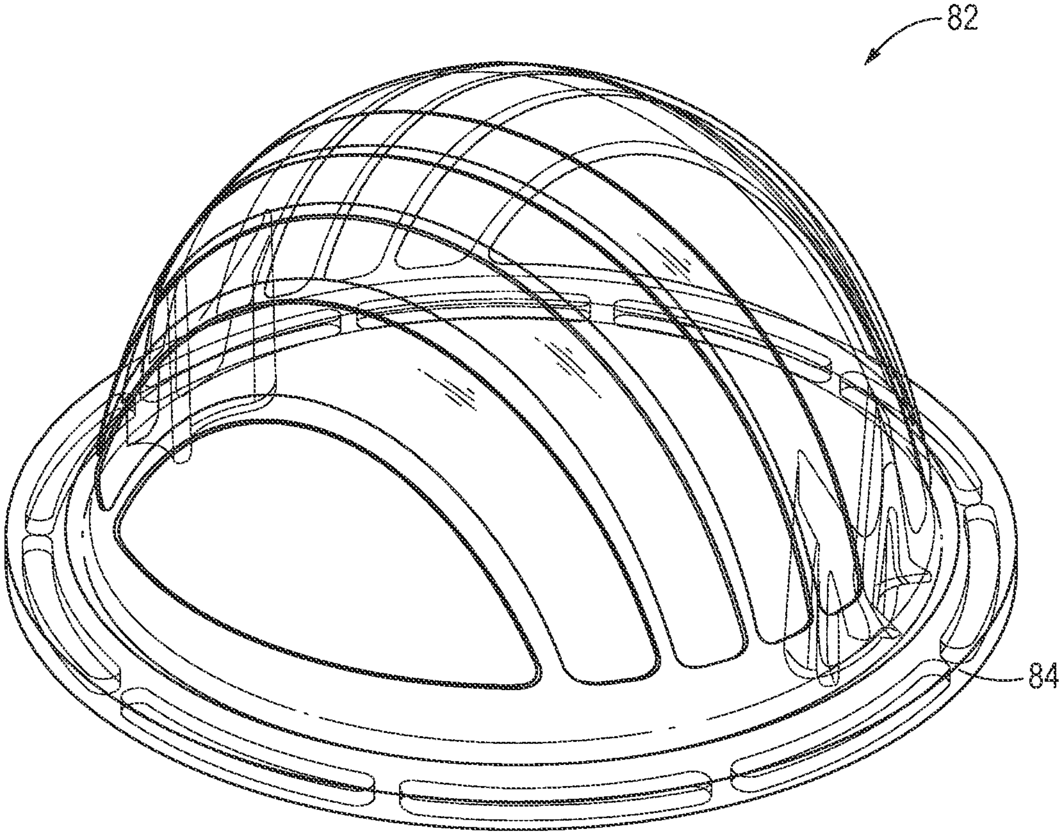
FIG. 11 is a perspective view of a bubble or globe of a core.

Referring more particularly to FIG. 11, a dome 82, or bubble 82, may be comprised of any suitable material. Generally, a suitable material is somewhat flexible and durable, i.e., polyurethane, silicone, polymer, plastic, rubber and similar compounds. A dome 82 may be translucent or opaque, or any desired color. A dome 82 may include a dome rim 84, or bubble rim 84 or flange 84, which dome rim 84 may serve as a base or foundation for the dome 82. A dome 82 may include any suitable or desired texturing, which texturing may provide an indication of wheel 112 alignment, or some other feature of the core 50. A dome 82 may protect the wheel configuration from contamination or damage, and the dome 82 may protect a user of the system 10 from harm that could be caused by the wheels while the system 10 is in operation.

Figure 12:
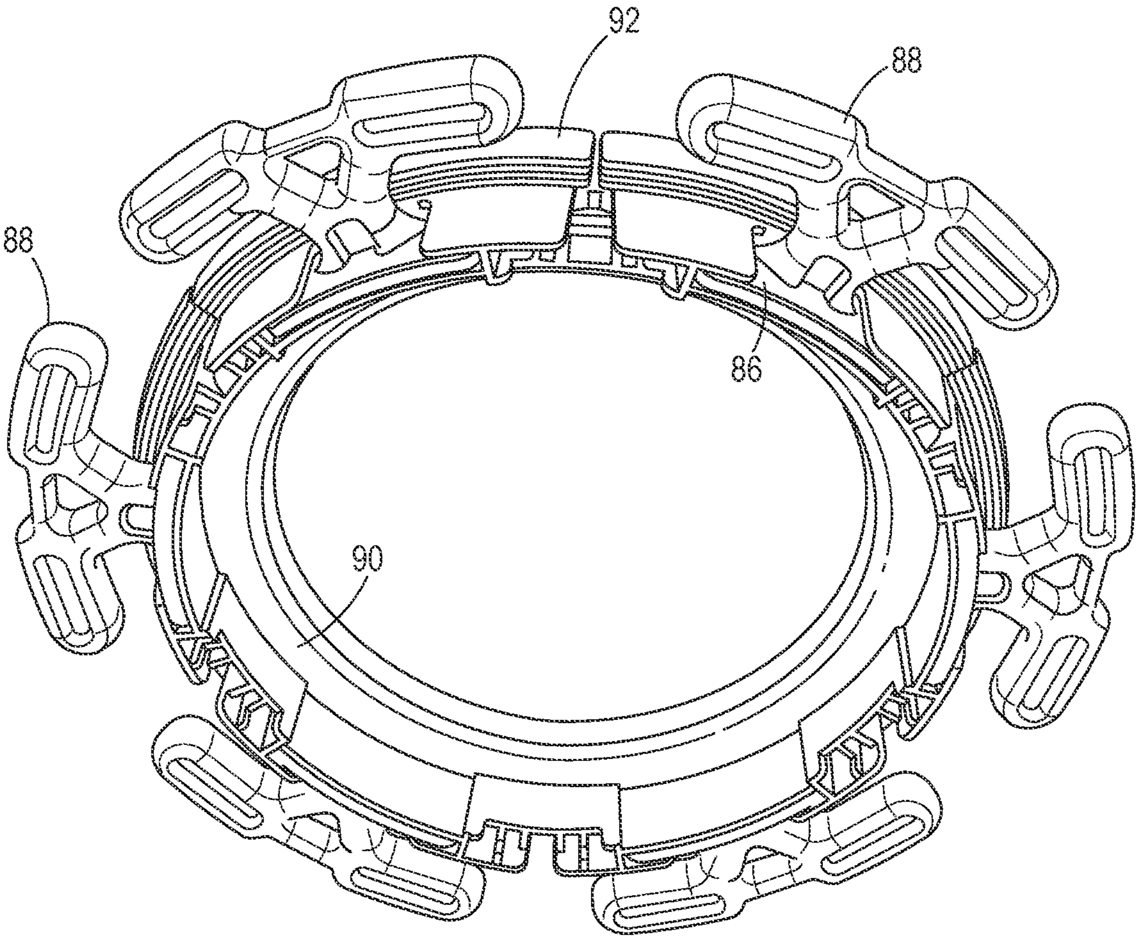
FIG. 12 is an upwards, perspective view of a bezel with handles of a core.

Referring more particularly to FIG. 12, a bezel 90 may include various structures and configurations. A bezel 90 may be comprised of any suitable material, i.e., plastic, polymer or the like. Generally, a suitable material will be strong and somewhat rigid to support other structures. A bezel 90 may include handle connections 86, which handle connections 86 may serve as connection points for handles 88. A bezel 90 may include multiple handles 88, generally spaced evenly and radially around the bezel 90. A bezel 90 may include a lighting array 92, or a lighting fixture 92.

Figure 13:
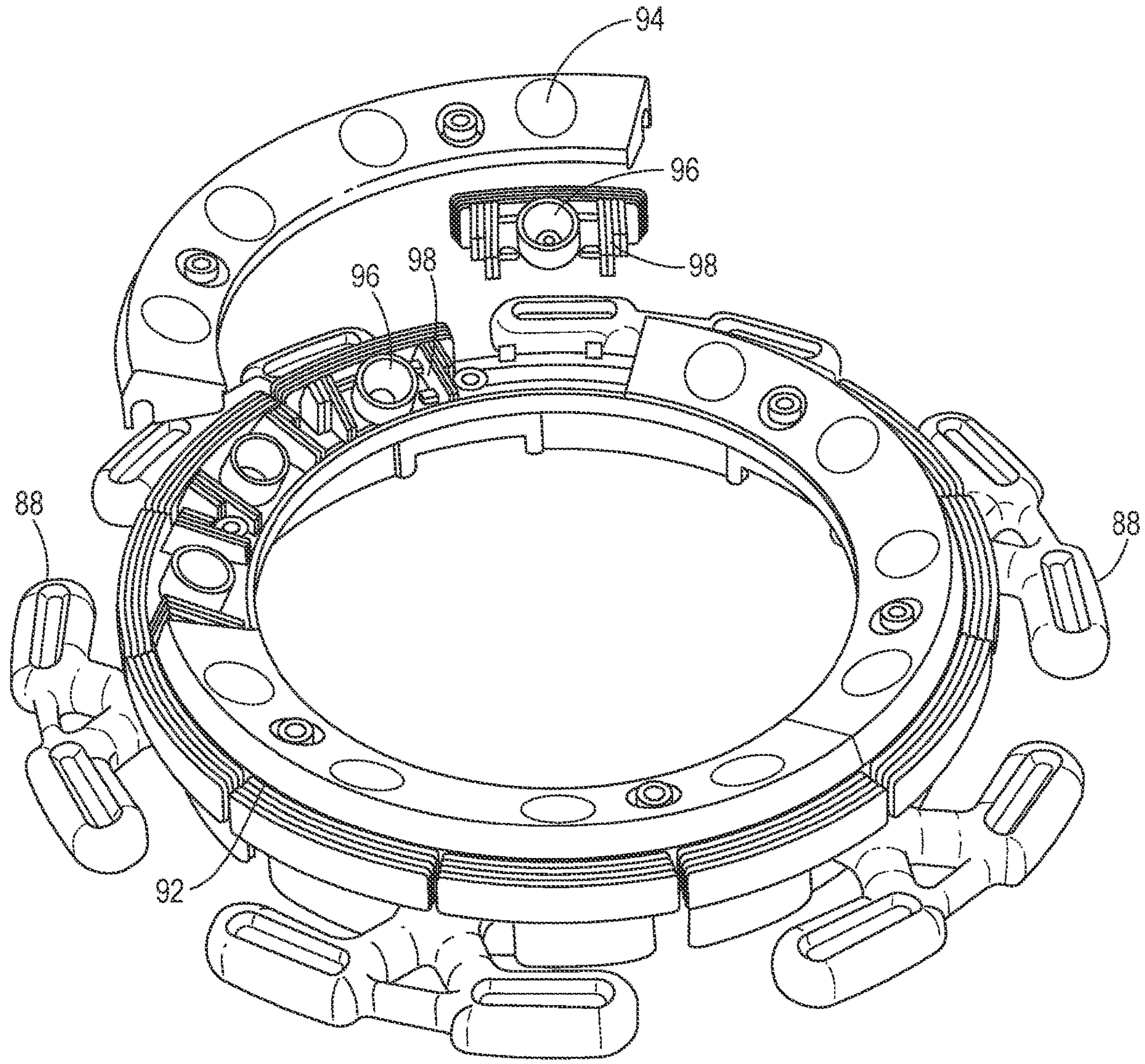
FIG. 13 is a downwards, perspective view of a bezel with a light array, and a partially exploded view of a light array.

Referring more particularly to FIG. 13, a bezel 90 may include a lighting array 92, which lighting array 92 may be comprised of various structures and configurations. A lighting array 92 may include a lens 94, which lens 94 may serve as a cover over a light source 96 and a heat sink 98. A lens 94 may be comprised of any suitable material, i.e., plastic, polymer or the like. Generally, a suitable material will be somewhat rigid and translucent to allow light to pass through the lens 94. A lighting array 92 may include a heat sink 98 around a light source 94, which heat sink 98 may be formed to help make sure the light source 96 does not become too hot. A light source 96 may provide various types of light, i.e., UV light, IR light, visible light or the like. A light source 96 may be an LED Infrared light source. Light from a light source 96 may provide various benefits to a user of the system 10. For example, UV light may be used to help a body produce vitamin D, provide anti-bacterial affects, or treat psoriasis, eczema, jaundice, and localized scleroderma. IR light at approximately 660 nm and/or at approximately 850 nm may stimulate healthy skin facia and muscle cells. Visible light may be used to help illuminate the skin surface, or to warm the skin. A lighting array 92 may comprise multiple light sources 94 where all light sources 94 provide the same type or light, or different light 94 provide different types of light. A lighting array 92 may comprise infrared LED light sources 94 in the near range and far range radiation, which has been shown to be penetrative and therapeutic to the skin, facia, and/or muscle cells.

Figure 14:
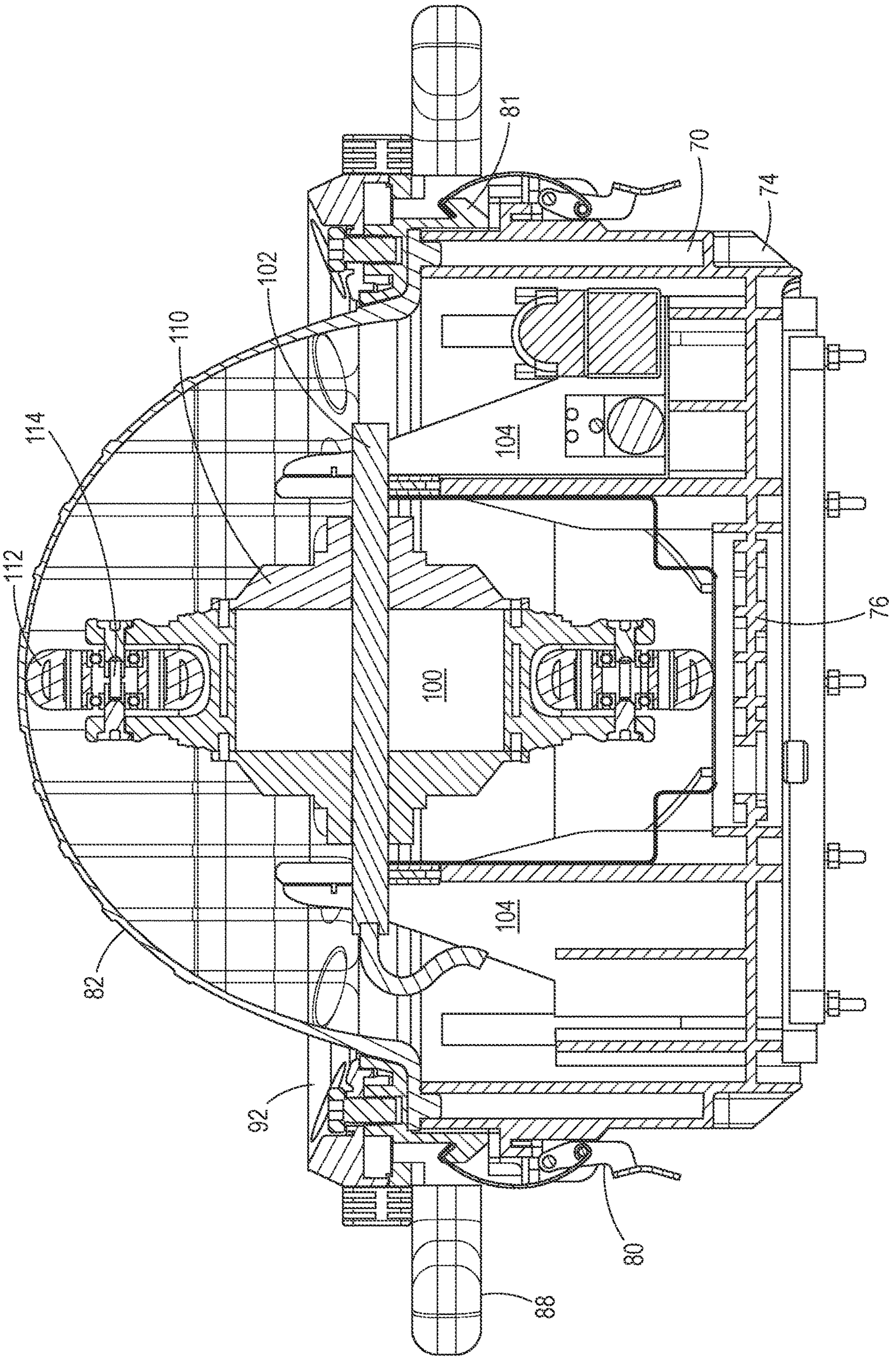
FIG. 14 is a cross-section view of a core.

Referring more particularly to FIG. 14, a core 50 may be comprised of various structures and configurations. A vessel 70 may include motor mounts 104, or mounts 104, which mounts 104 provide a foundation and support for a hub motor 100. A hub motor 100 may provide a means for rotating a sprocket relative to a motor axle 102. A hub motor 100 may include a motor axle 102, which motor axle 102 provides for and facilitates rotation of the sprocket 110 around the motor axle 102. A sprocket 110 may include wheels 112 rotatably attached to the sprocket via wheel axles 114. In some embodiments, a hub motor 100 may be described as a motorized rotary sprocket with wheels connected to the sprocket.

Figure 15:
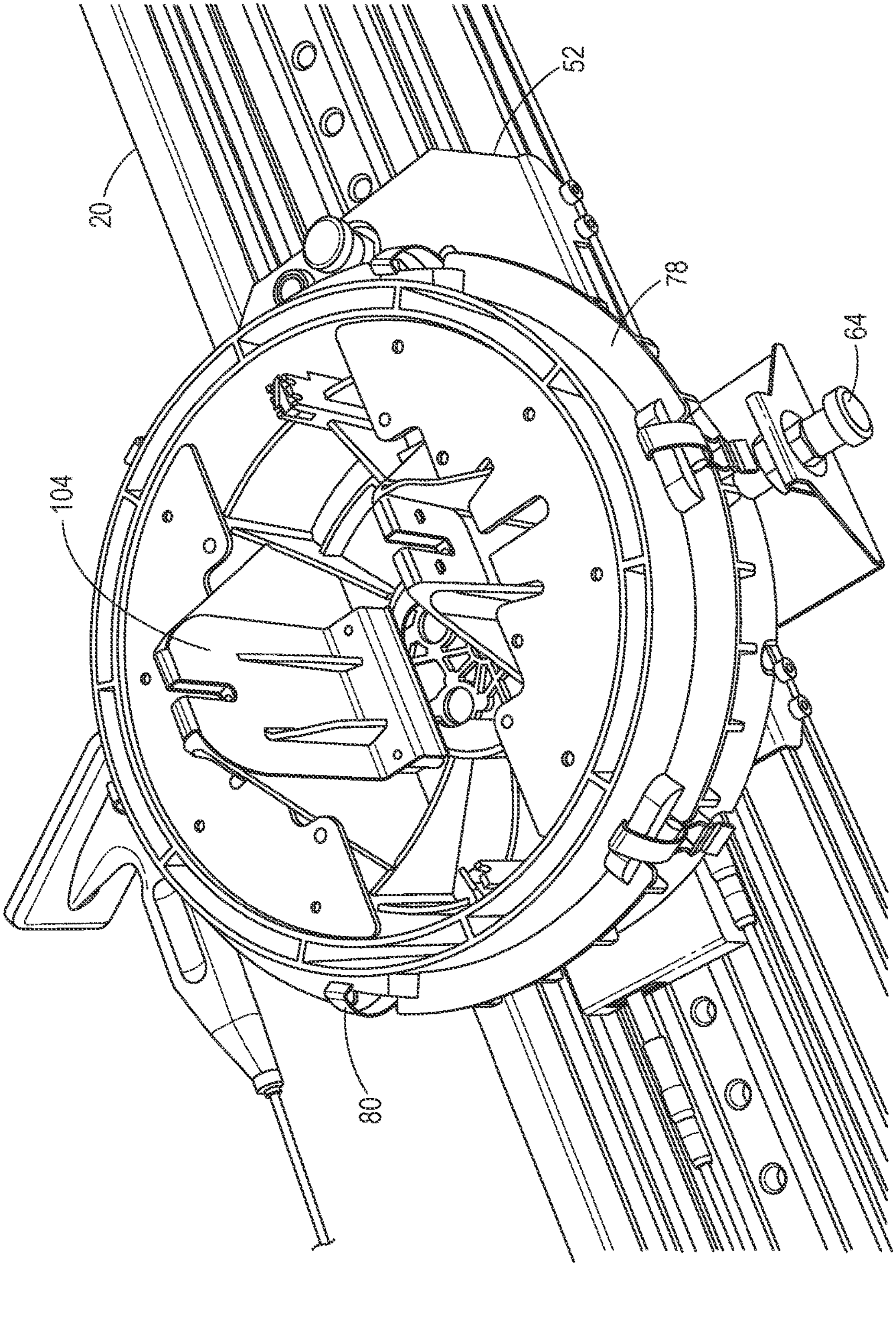
FIG. 15 is a perspective view of an open vessel or bowl of a core.

Referring more particularly to FIG. 15, a vessel 70 may be operably connected to a carrier 52, which carrier 52 is operably connected to a rail 20. The vessel 70 may include motor mounts 104, or mounts 104, which mounts 104 provide a foundation for mounting a hub motor 100 within the vessel 70.

Figure 16:
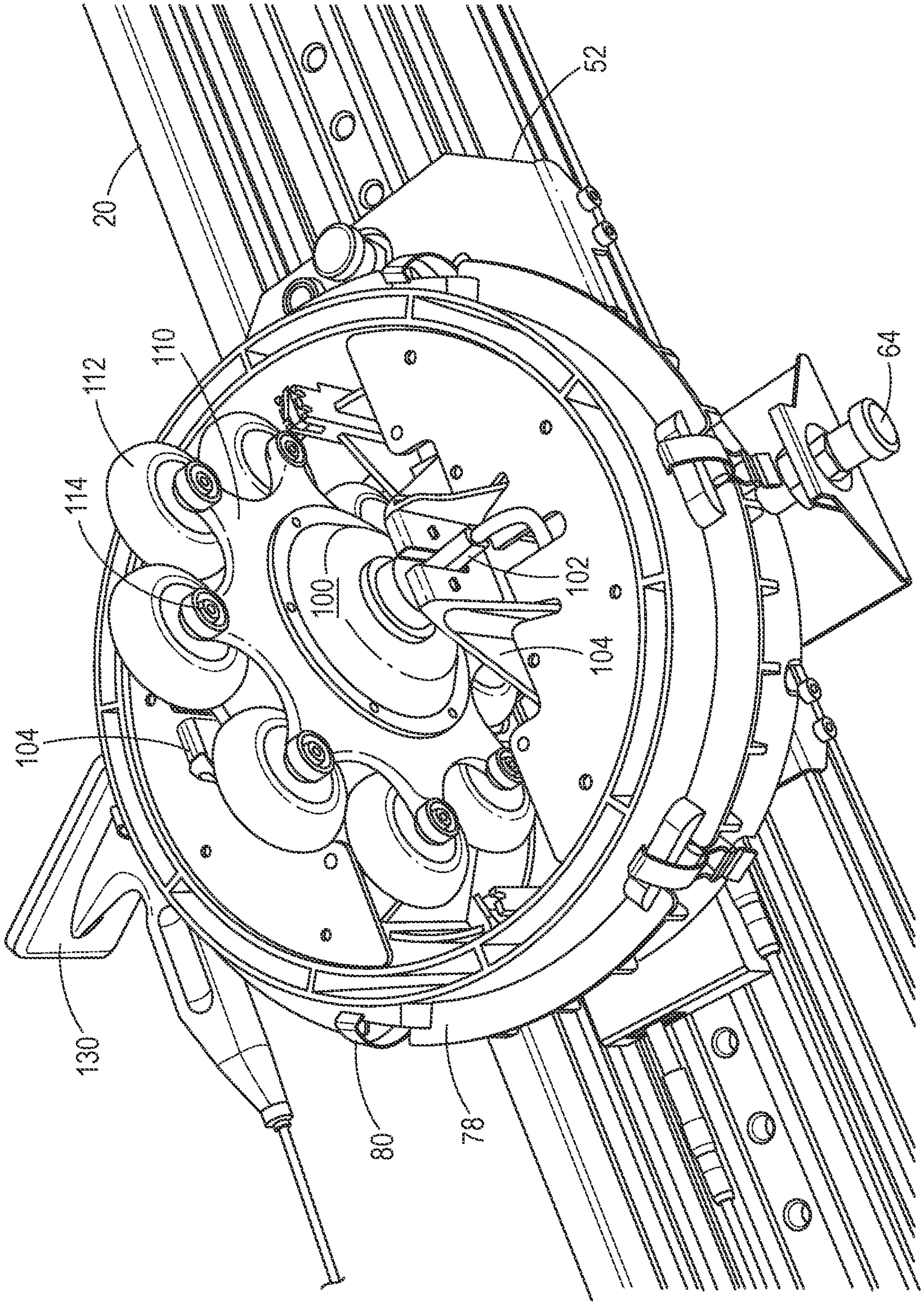
FIG. 16 is a perspective view of an open vessel or bowl of a core with a hub motor and wheels.

Referring more particularly to FIG. 16, a vessel 70 may contain a hub motor 100. The hub motor 100 may be inserted into and contained within the vessel 70 using mounts 104 in a manner that allows the motor axle 102 to operate as intended. A hub motor 100 may be operably connected to a sprocket 110. Wheels 112 may be operably connected, rotatably connected, to the sprocket 110 via wheel axles 114.

Figure 17:
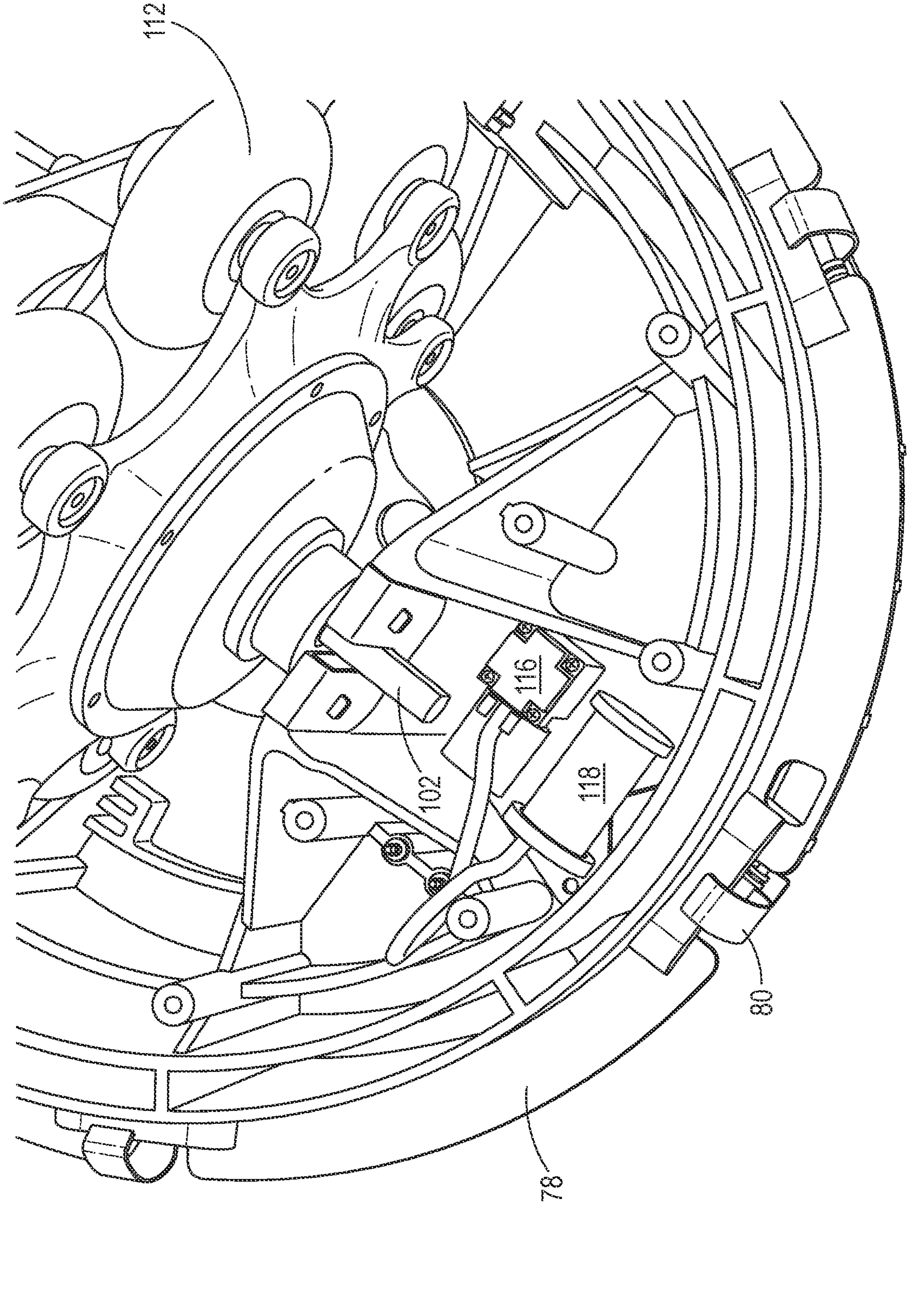
FIG. 17 is a top view of an open vessel or bowl of a core with a pump and valve configuration.

Referring more particularly to FIG. 17, a vessel 70 may include a pump 116 and a valve 118. A pump 116 and a valve 118 may be operably connected to the vessel 70 and contained within the vessel 70. In operation, the pump 116 and valve 118 may be used to pressurize and depressurize the cavity that is formed when a dome 82 is secured to the vessel 70 by the securement of a bezel 90 using vessel latches 80. A dome rim 84 may be secured to a vessel rim 78 in a manner that creates an air-tight seal, thus enabling the pressurization of the cavity formed by the vessel 70 and the dome 82, which pressurization may be provided by the pump 116 and the valve 118 components contained within the cavity. Generally, a pressure of approximately 0.02 psi to approximately 2.0 psi may be maintained within the cavity or chamber. A low pressure range may be described as approximately 0.2 psi to approximately 0.8 psi. A medium pressure range may be described as approximately 0.9 psi to approximately 1.4 psi. A high pressure range may be described as approximately 1.5 psi to approximately 2.0 psi. In certain embodiments, the pressure may be as high as 4.0 psi. The pressurization of the cavity allows the dome 82 to feel softer or more solid to a user depending on the amount of pressurization. The more pressurization of the cavity, the more solid the dome will feel, and the shallower the wheeled sprocket may penetrate the body. Conversely, the lower the pressurization of the cavity, the deeper the wheeled sprocket may penetrate the body.

In one embodiment, the bezel 90 being latched down to the vessel 70 via vessel latches 80 with the dome rim 84 between the vessel rim 78 and bezel 90 may create a sealed cavity or chamber. The cavity or chamber may be pressurized and adjusted via an electric pump 116 (or Schrader valve) and electric valve 118. The process may be controlled by the controller 130. The pump 116 may add pressure and the valve 118 may reduce pressure. The pressure inside the cavity or chamber may keep the dome 82 from contacting the sprocket 110, so that the dome 82 only contacts the wheels 112. The pressurized dome 82 may allow for adjustment of the acuteness of the wheeled sprocket felt thru the dome 82. The pressure may be adjustable by a user via the controller 130 and/or various programmable settings.

In operation, the higher the pressure in the cavity, the less acute the massage therapy, or the less the user would feel the wheel rotation. Conversely, the less pressure in the cavity, the more acute the massage therapy, or the more the user would feel the wheel rotation. The pressurized dome 82 may also provide a safety feature for the system 10 in that it completely seals off the rotating hub motor and wheeled sprocket, thereby removing any possibility that a user's hair, clothing, skin, body part, or the like could be pulled, pinched, or entangled in the wheeled sprocket. In one embodiment, if the dome 82 becomes compromised, is perforated or cut, or loses pressure below a minimum pressure dictated by an onboard pressure sensor/programming, the system 10 or core 50 may shut itself off completely and will not operate until repaired and reset. Generally, any pressure reading below 0.2 psi will result in the system 10, core 50, and/or hub motor 100 being shut down.

In one embodiment, a dome 82 may not be pressurized and is simply formed and positioned so that its shape provides a similar safety barrier. In one embodiment, a hub motor and wheeled sprocket may be utilized without a dome 82, with the wheeled sprocket exposed. However, alternative safety features should be utilized with such an embodiment. For example, and not by way of limitation, power cut-off switches may be mounted to the vessel 70, and located at the top and bottom edge of the vessel top 79 where the wheeled sprocket emerges from the vessel 70, or such power cut-off switches could be mounted along the circumference of the vessel top 79, or such power cut-off switches could be mounted to the bezel 90, or any appropriate combination of such switches. At the location where the wheeled sprocket is nearest the vessel top 79 and/or bezel 90 and/or dome 82, if any object or body part were to become jammed into the crease between the wheels and vessel top 79, or vessel 70, or bezel 90, or dome 82, a lug feature on the dome 82 or on the bezel 90 or on the vessel 70 would contact the cut-off switch and cut power to the hub motor 100, thus stopping the wheeled sprocket from rotating.

Figure 18:
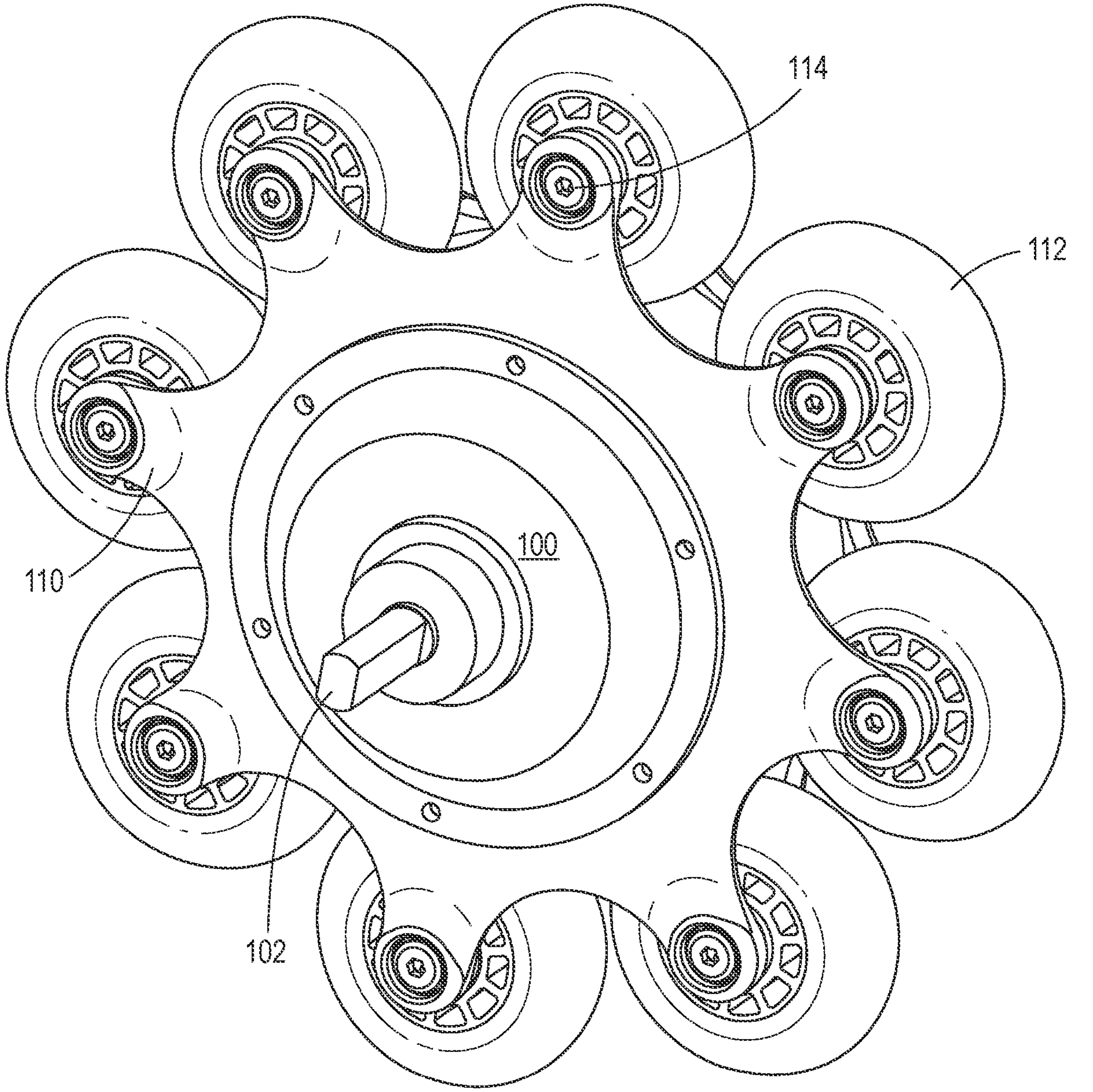
FIG. 18 is a perspective view of a hub motor with wheels configuration.

Referring more particularly to FIG. 18, a hub motor 100, or wheeled sprocket, may be comprised of various structures. A hub motor 100 may include a motor axle 102, which motor axle 102 may provide means for rotation of a sprocket 110 operably connected to the hub motor 100. A sprocket 110 may include multiple wheels 112, which wheels 112 are generally arranged in a linear fashion around the sprocket 110 and contact the dome 82. In operation, the wheels 112 will provide the massage therapy to a user of the system 10. The hub motor 100 may be operably connected to rotate the sprocket 110. The sprocket 110 may then rotate the wheels 112, which wheels 112 may also rotate in relation to the sprocket 110 via wheel axles 114. The wheels 112 may be configured to provide ultra-low friction, or zero resistant rotation against the force of a body of a user being pressed on by the wheels 112, while still providing the linear pressure, rolling, kneading and/or milling action. A "wheeled sprocket" may be attached to a geared hub electric motor 100, which may be described as the essence of the core 50 in some embodiments.

A hub motor 100, or wheeled sprocket, may have a diameter of approximately fourteen (14) inches, or approximately 35 cm. This approximate diameter may be considered a good compliment to the musculature and architecture of the human body. A larger diameter could be too flat to be effective and a smaller diameter could be too sharp to be comfortable. The diameter described here should be considered an example and not a requirement. The diameter may vary depending on the intended use and desired outcome.

Figure 19:
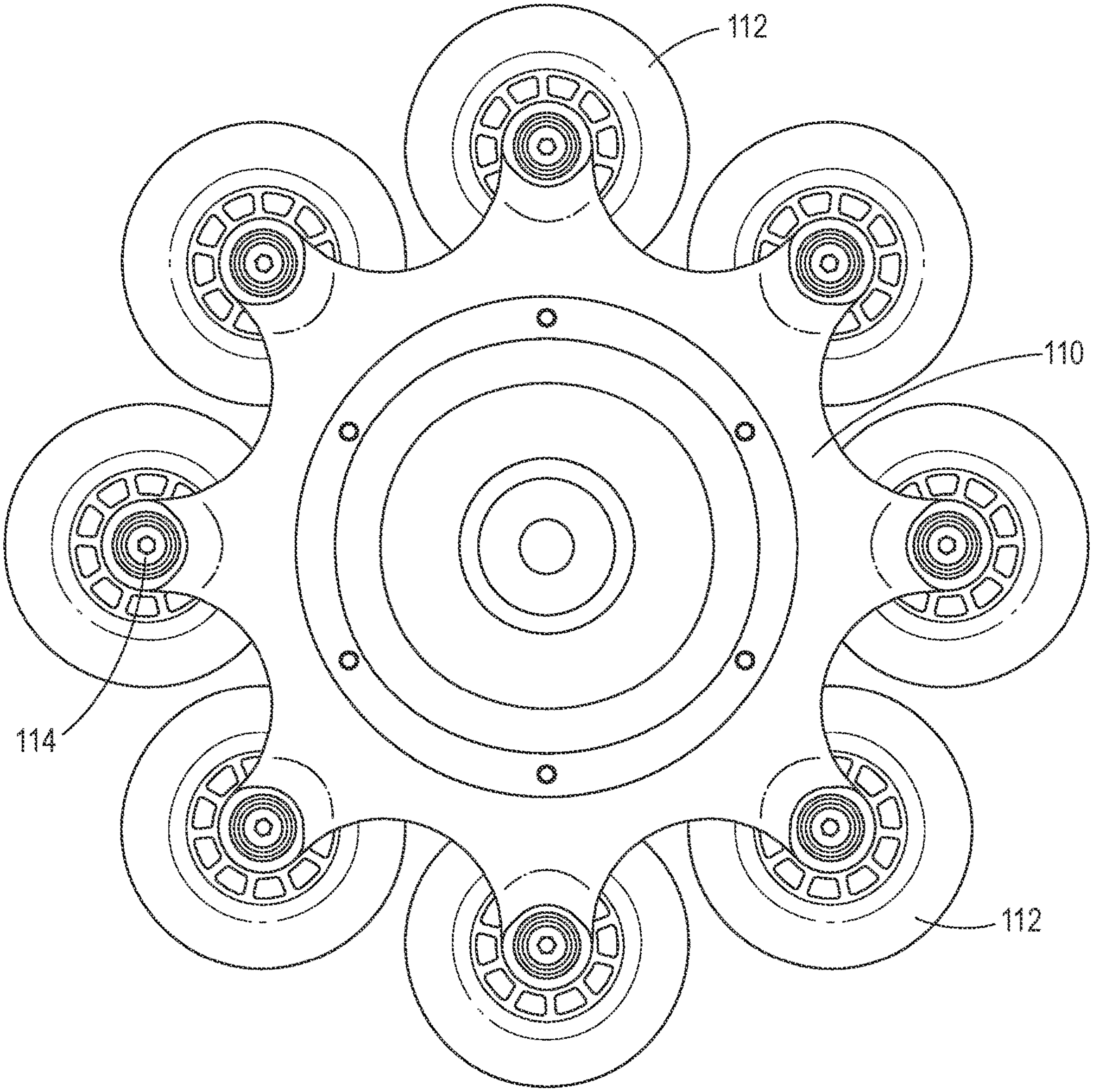
FIG. 19 is a side view of a hub motor with wheels configuration.
Figure 20:
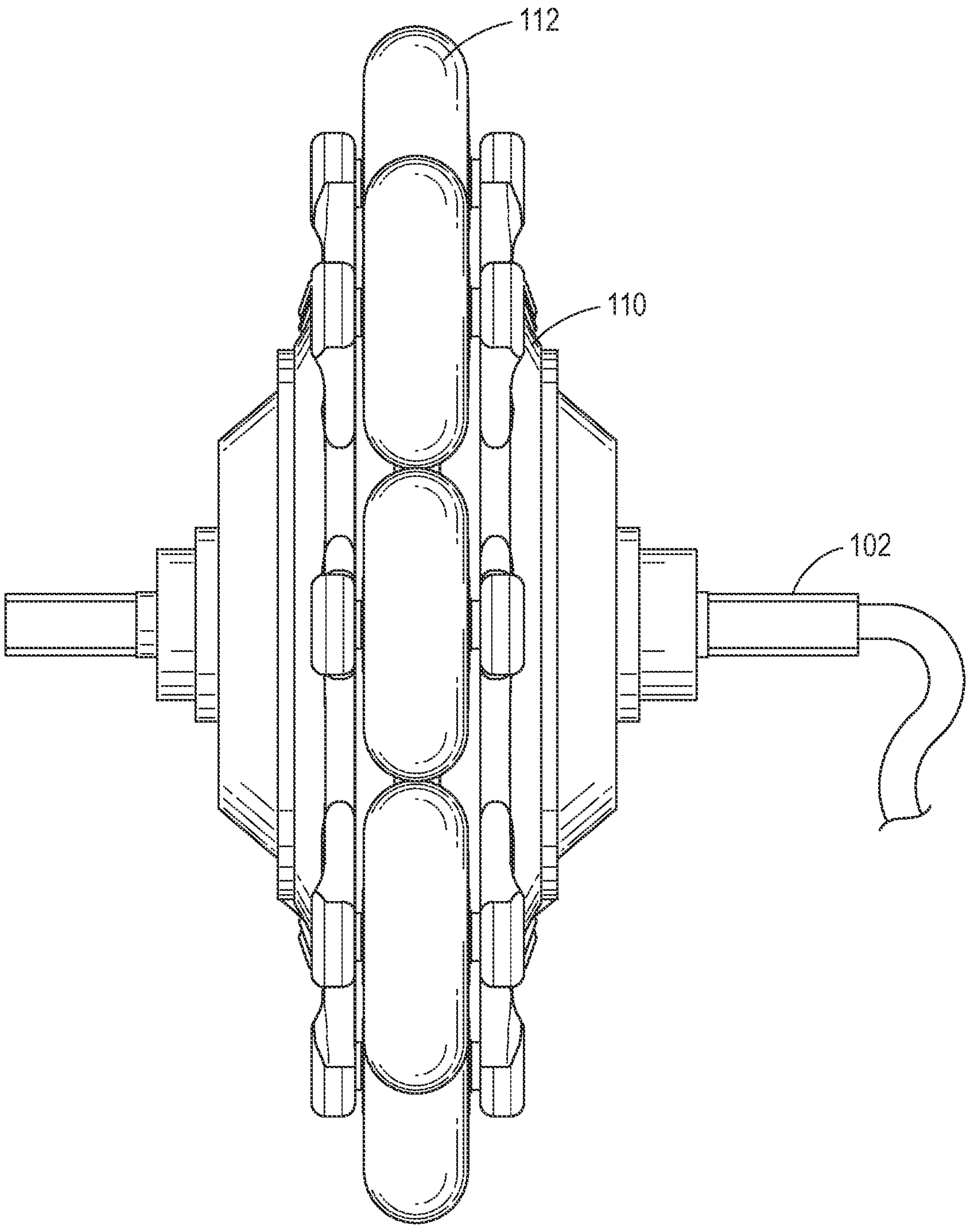
FIG. 20 is a frontal view of a hub motor with wheels configuration.

Referring more particularly to FIGS. 19 and 20, a sprocket 110 may include multiple wheels 112 operably connected, or rotatably connected, to the sprocket 110 via wheel axles 114. In one embodiment, the wheels 112 may be arranged and positioned around the sprocket 110 in a linear fashion. In one embodiment the wheels 112 may be described as "inline roller blade" type wheels (solid polyurethane tire, with plastic wheel hub and roller bearings), but could be a metal, pneumatic or elastomeric wheel or other material or diameter or width or shape (for example octagonal as opposed to round). In another embodiment, a sprocket 110 could have lobes in place of wheels.

Figure 21:
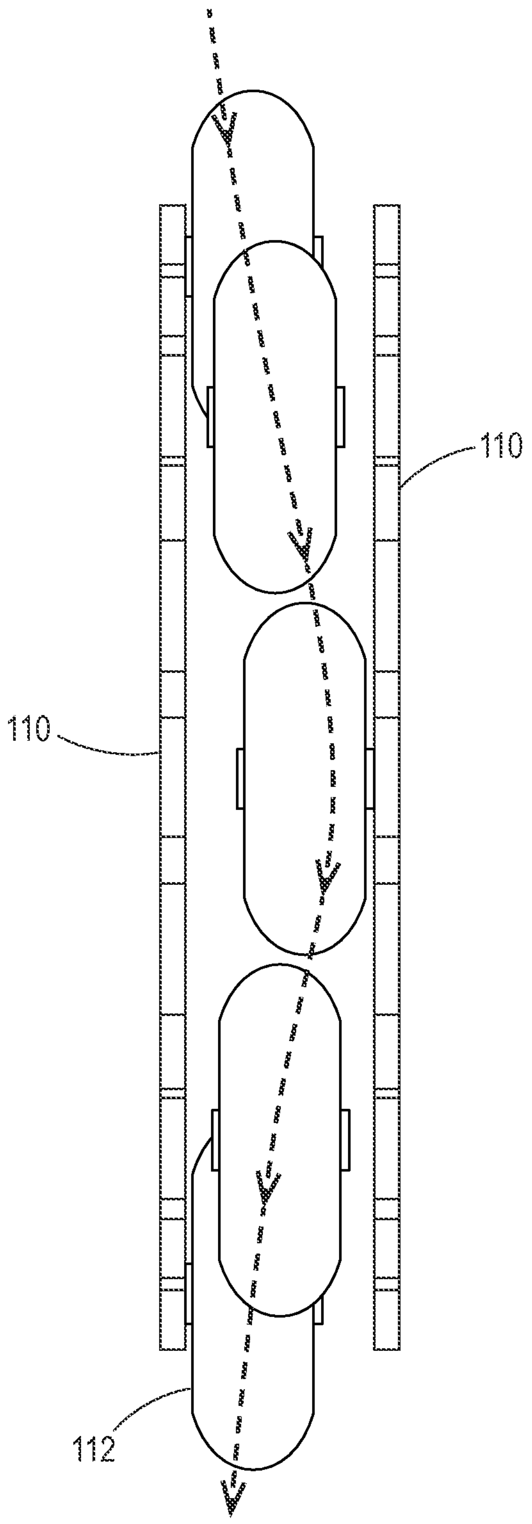
FIG. 21 is a frontal view of a hub motor with a staggered configuration of wheels.

Referring more particularly to FIG. 21, a sprocket 110 may include wheels 112 that are arranged and positioned around the sprocket 110 in a staggered fashion, where the wheels 112 are not connected to the sprocket 110 in a linear fashion. An arrow in FIG. 21 shows a path the wheels 112 may take during operation. A staggered configuration of wheels 112 may be utilized to provide a different type of massage. A staggered configuration of wheels 112 may provide a wider and vacillating massage interface surface to a user.

Figure 22:
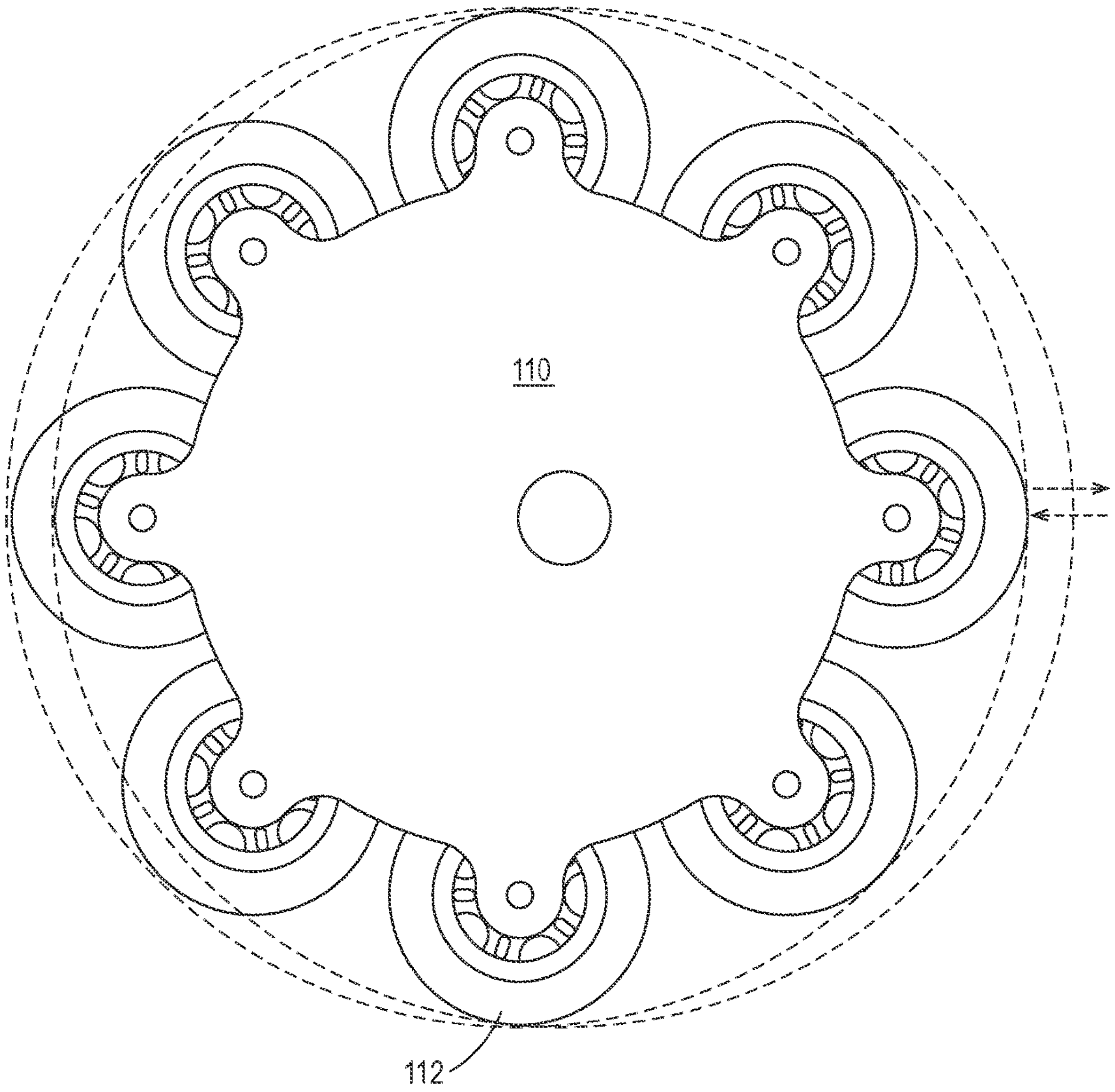
FIG. 22 is a side view of a hub motor with wheels with an off-center axis configuration.

Referring more particularly to FIG. 22, in one embodiment, a sprocket 110 may include an off-center axis. A sprocket 110 may have wheels 112 rotatably attached around the sprocket 110. In operation, the off-center axis may provide a back-and-forth, pulsating motion to wheels 112, as shown by the arrows in FIG. 22.

Figure 23A:
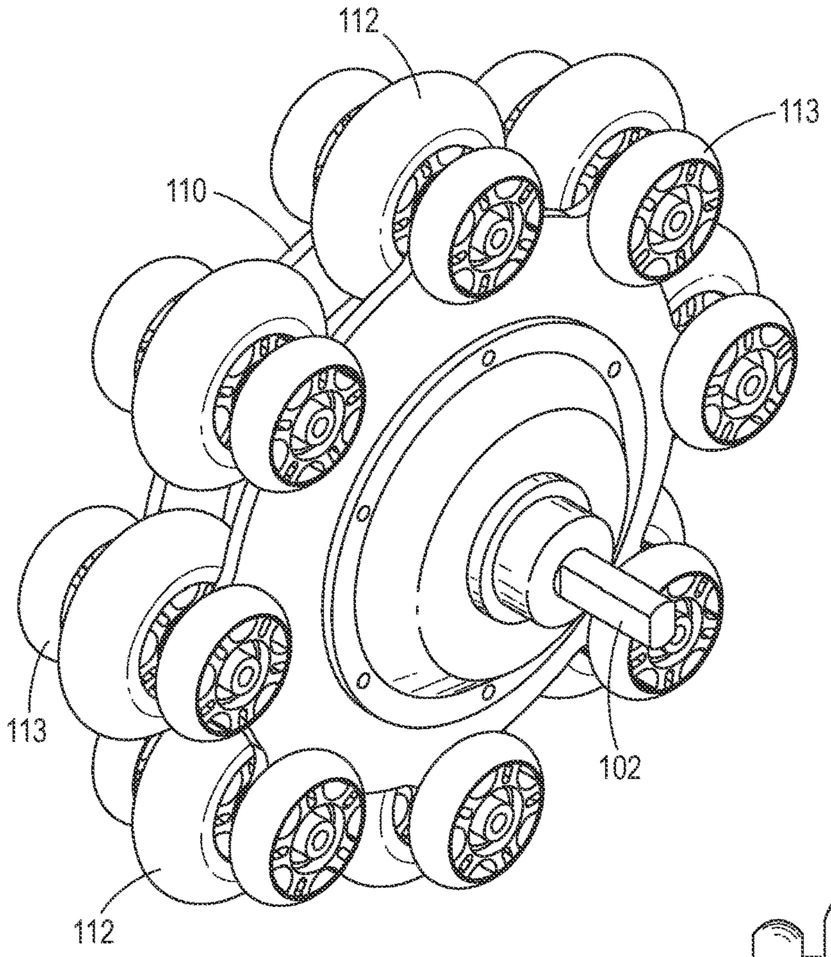
FIG. 23A is a perspective view of a hub motor with multiple rows of wheels configuration.
Figure 23B:
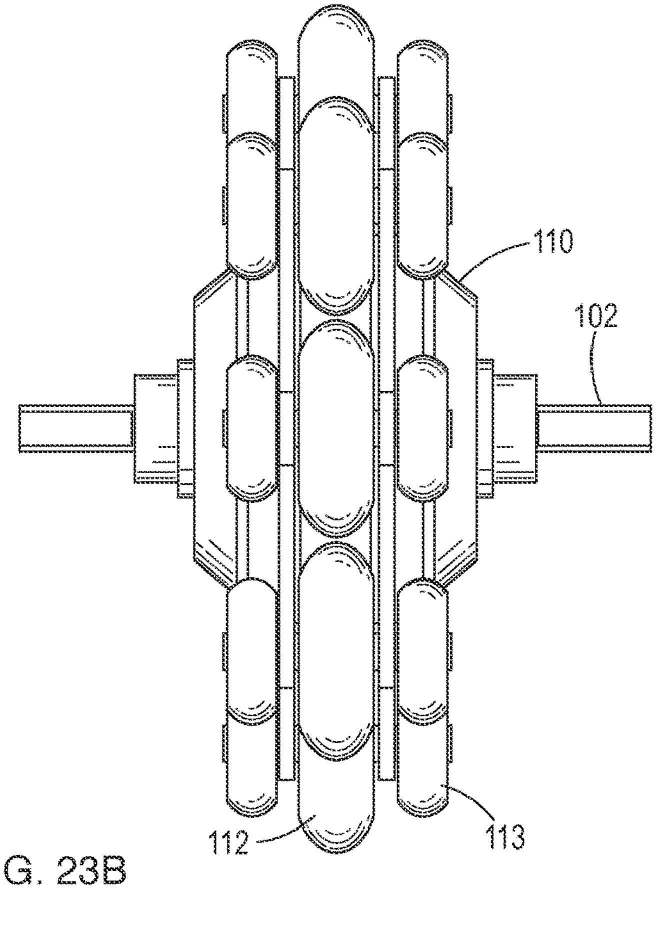
FIG. 23B is a frontal view of a hub motor with multiple rows of wheels configuration.

Referring more particularly to FIGS. 23A and 23B, in one embodiment, a sprocket 110 may include primary wheels 112 and secondary wheels 113. Primary wheels 112 and secondary wheels 113 may be operably connected, rotatably connected, to the sprocket via wheel axles 114. Secondary wheels 113 may be included on either side or both sides of primary wheels 112. Generally, secondary wheels 113 may be of a smaller diameter as compared to primary wheels 112. In operation, a sprocket configuration that includes both primary wheels 112 and secondary wheels 113 may provide a wider massage interface surface that can also provide different and/or varying depths. For example, primary wheels 112 may penetrate a user's soft tissues more so than secondary wheels 113. Also, secondary wheels 113 may protect the sprocket 110 from ever touching the dome 82.

Figure 24:
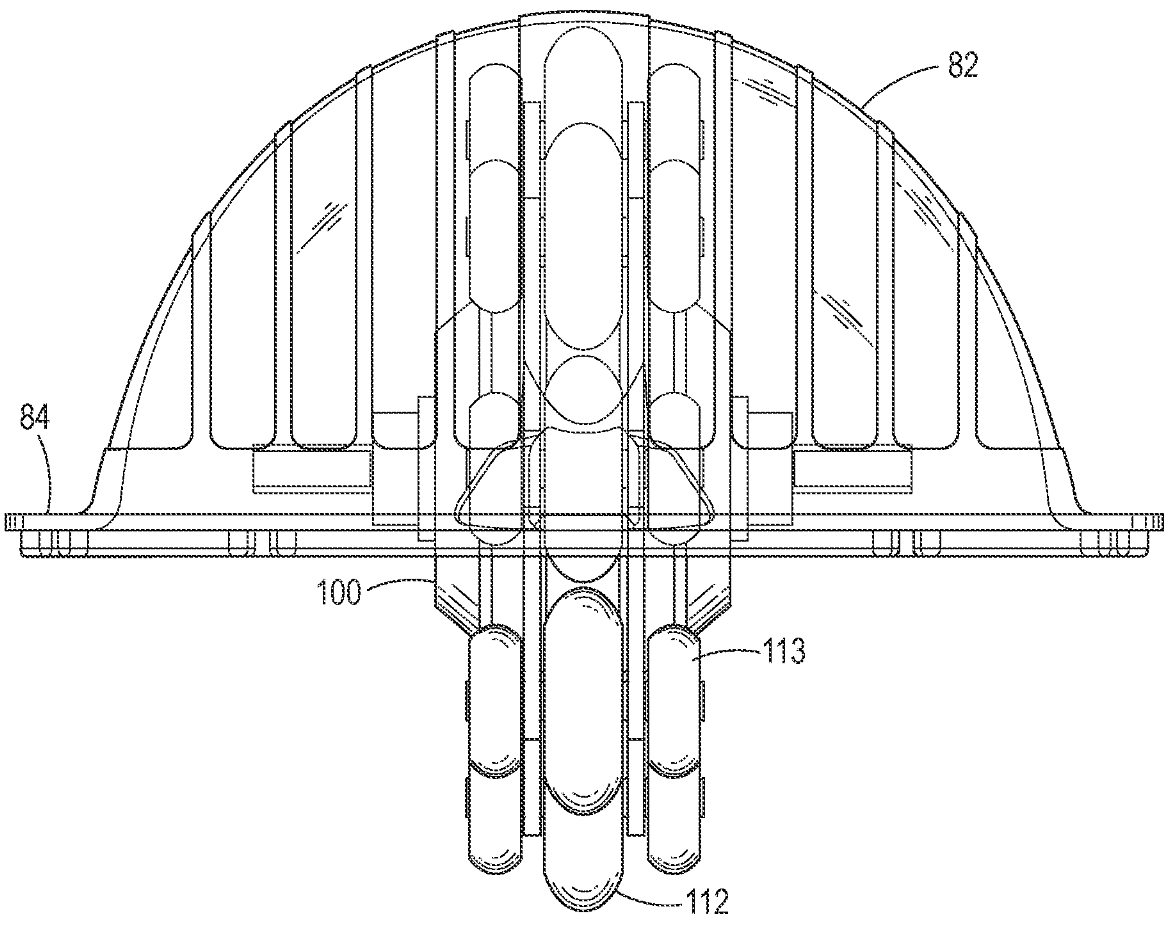
FIG. 24 is a frontal view of a hub motor with multiple rows of wheels configuration and a bubble or globe.

Referring more particularly to FIG. 24, various sprocket and wheel configurations may still be positioned under and within a dome 82. For example, a hub motor 100 and sprocket with primary wheels 112 and secondary wheels 113 may be positioned under and within a dome 82. Thus, the dome 82 protects the wheel configuration from contamination or damage, and the dome 82 protects a user of the system 10 from harm that could be caused by the wheels.

Figure 25:
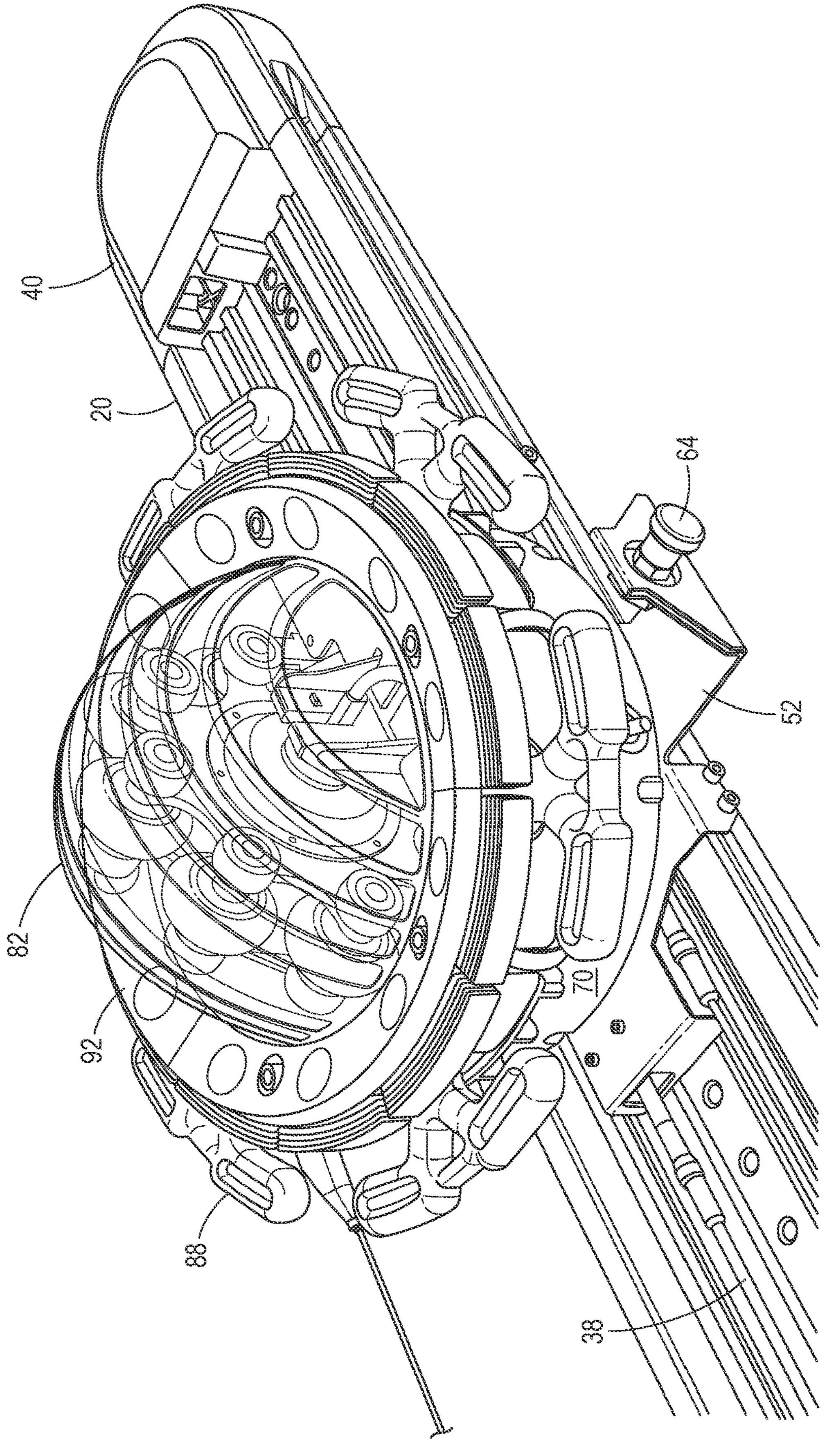
FIG. 25 is a perspective view of a core with a multiple rows of wheels configuration with the core connected to a rail.

Referring more particularly to FIG. 25, in one embodiment, a sprocket configuration having primary and secondary wheels may be contained within the cavity formed by the vessel 70 and the dome 82. The core 50 may be operably connected to a carrier 52, which carrier 52 is operably connected to a rail 20.

In various embodiments, the varied configurations of sprockets 110 and wheels 112 may be used individually or together. For example, a sprocket configuration as shown in FIG. 21 may be combined with a sprocket configuration as shown in FIG. 22. Thus, a massage experience that may be described as both undulating and pulsating may be provided.

It may also be noted that the system 10 may be designed to allow for the substitution of various types of sprockets 110, or various sprocket configurations, because different types of sprockets 110 may be mounted using the mounts 104 in the vessel 70. Thus, various types of sprocket configurations and wheel configurations may be considered interchangeable within the system 10. This may greatly increase the types of massage experiences that the system 10 can provide to a user.

Figure 26:
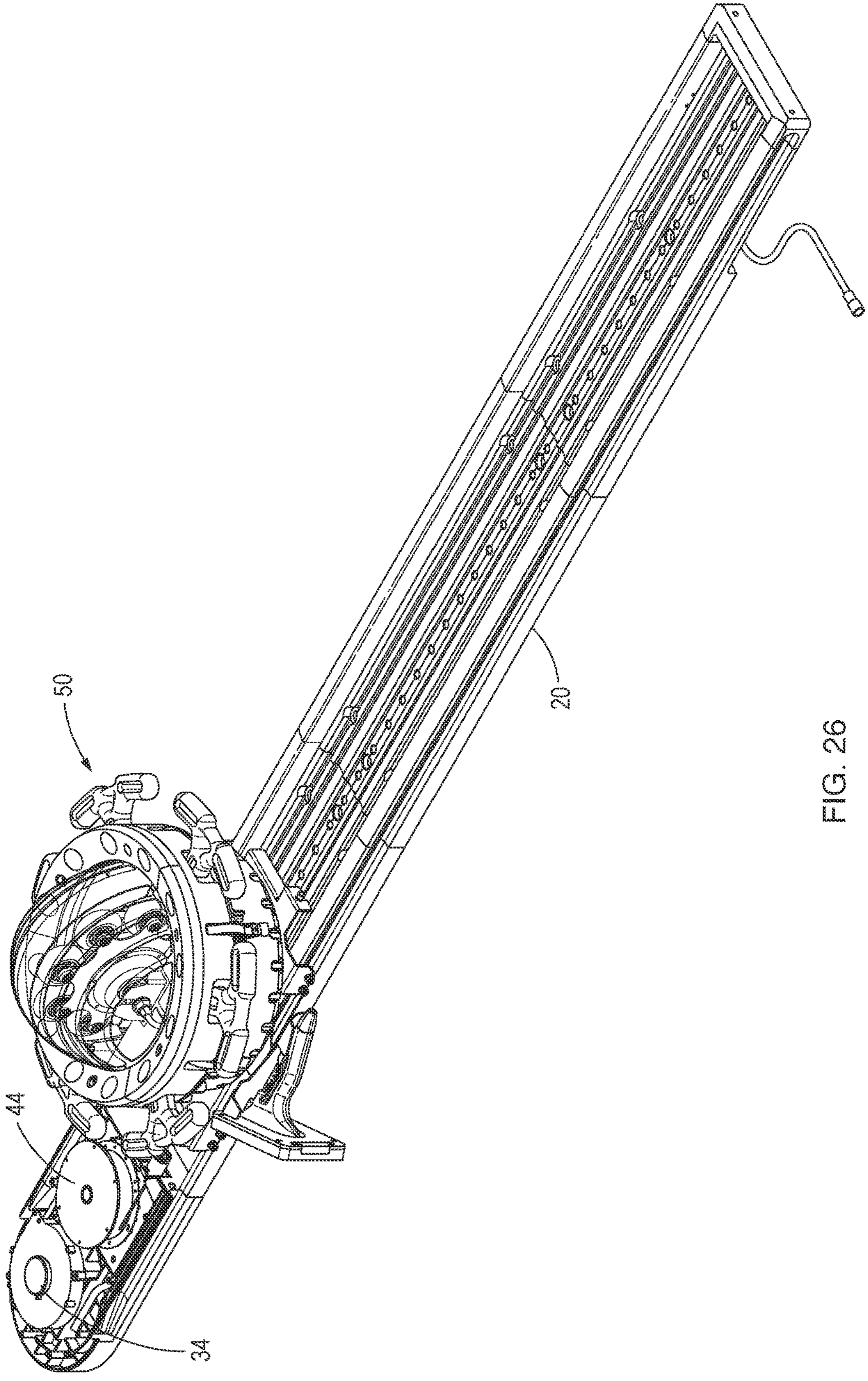
FIG. 26 is a perspective view of an embodiment of a rail system with internal structures at one end of the rail system.

Referring more particularly to FIG. 26, a rail 20 configuration may take various forms. For example, in one embodiment, a power reel 34 and a weight reel 44 may both be operably connected at one end of the rail 20. In such a configuration, a rail 20 could be mounted to a wall in such a manner that the bottom of the rail 20 is essentially flush with the floor. In another embodiment, a power reel 34 could be at the top (or distal) end of the rail 20, while a weight reel 44 could be at the bottom (or proximate) end of the rail 20. The embodiment or configuration of the rail 20 may be designed in any manner that is preferred by a user, or necessitated by the environment where the system 10 is going to be used.

Figure 27:
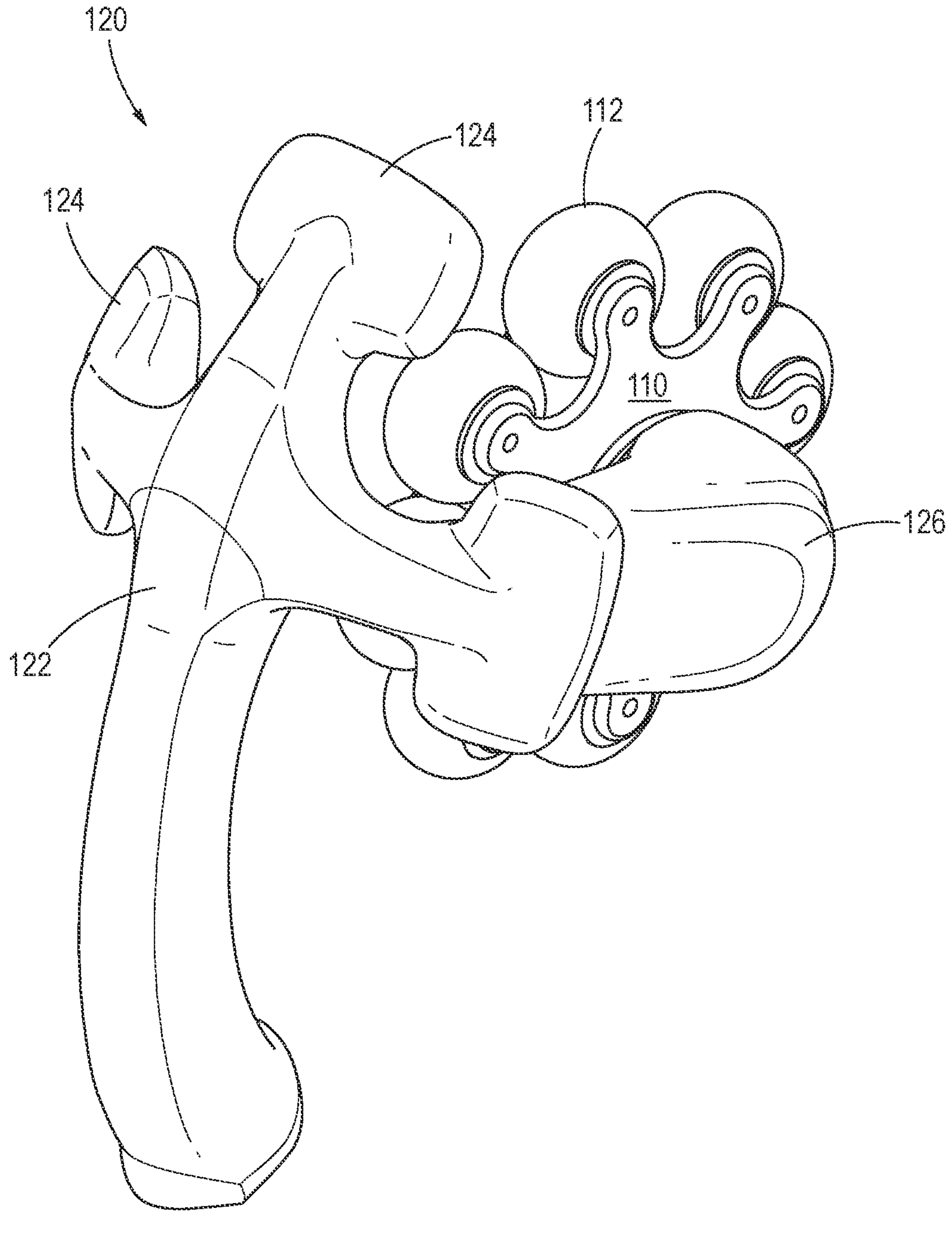
FIG. 27 is a rear perspective view of a hand-held massage therapy device.
Figure 28:
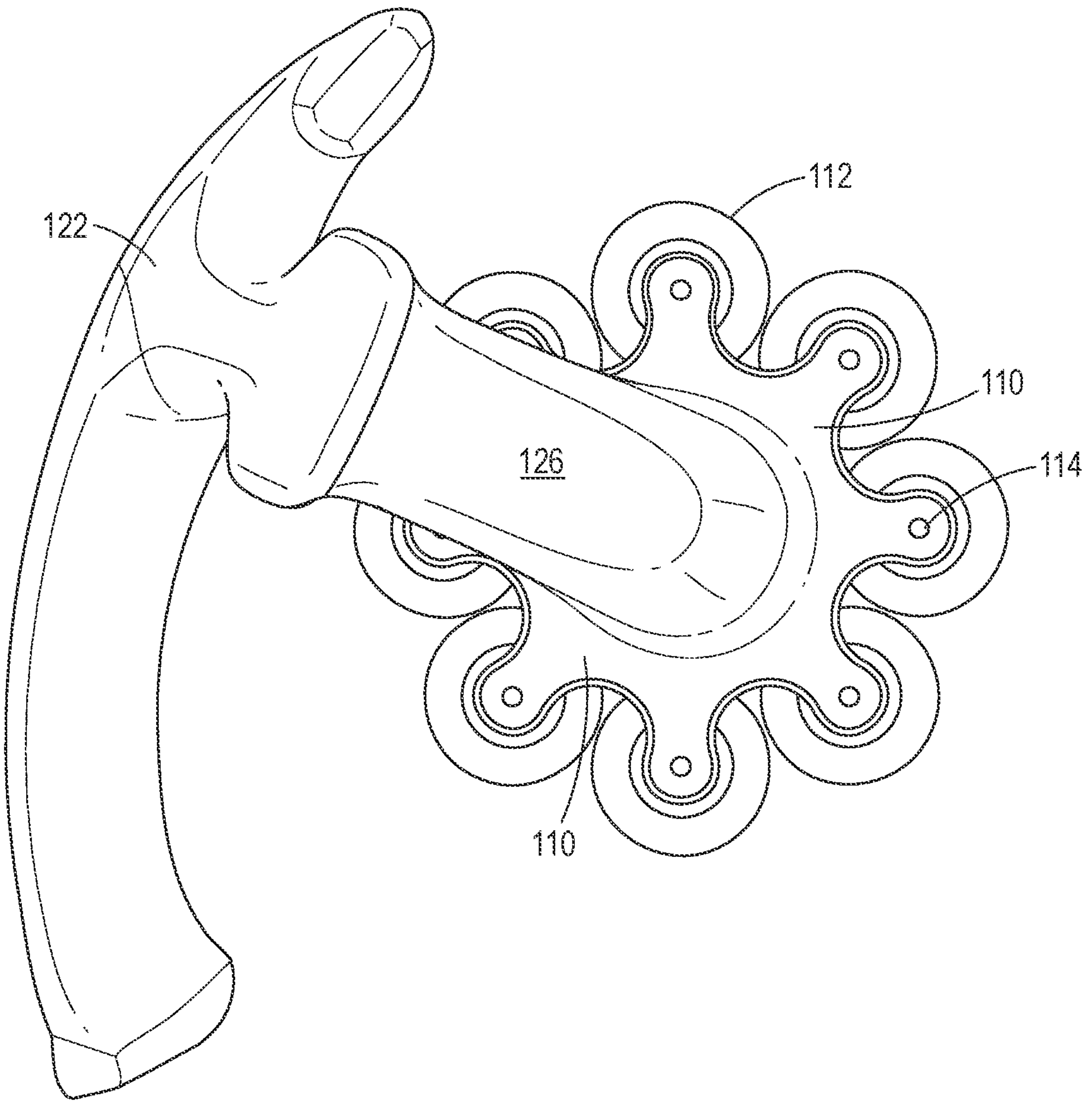
FIG. 28 is a side view of a hand-held massage therapy device.
Figure 29:
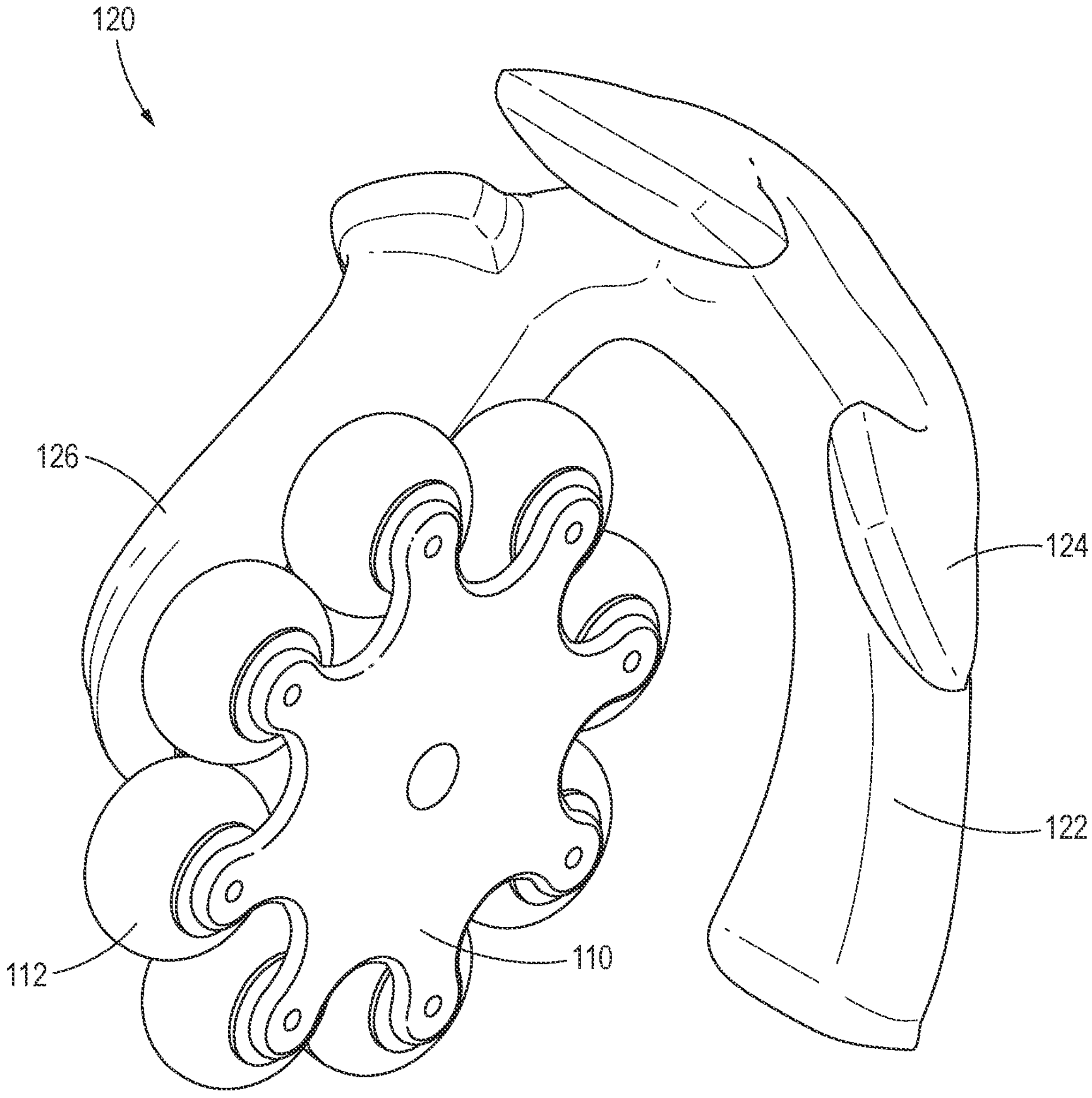
FIG. 29 is a front perspective view of a hand-held massage therapy device.

Referring more particularly to FIGS. 27-29, a sprocket 110 and wheel configuration may be provided in a hand-held configuration 120, or hand-held device 120. A hand-held device 120 may include a shaft 122, which shaft 122 may provide a primary structural support for other components. A hand-held device 120 may include grips 124 that a user may utilize to use and manipulate the hand-held device 120. A hand-held device 120 may include a stem 126, which stem 126 provides support and connection between the shaft 122 and the sprocket 110. In a hand-held device 120, a sprocket 110 may include wheels 112 operably connected, rotatably connected, to the sprocket 110 via wheel axles 114. In a hand-held device 120, a sprocket 110 may include wheels 112 operably connected to the sprocket 110 in a manner where the wheels 112 do not rotate in relation to the sprocket 110, although, the sprocket 110 would still rotate in relation to the stem 126.

Various embodiments of a hand-held device 120 may include the various sprocket and wheel configurations described herein. For example, and not by way of limitation, a hand-held device 120 may include a sprocket and wheel configuration like that described in FIG. 21, or like that described in FIGS. 23A and 23B, or combinations thereof. In operation, a hand-held device 120 may be used to perform peristaltic massage therapy, producing a peristaltic wave in the subject receiving physical therapy.

Figure 30:
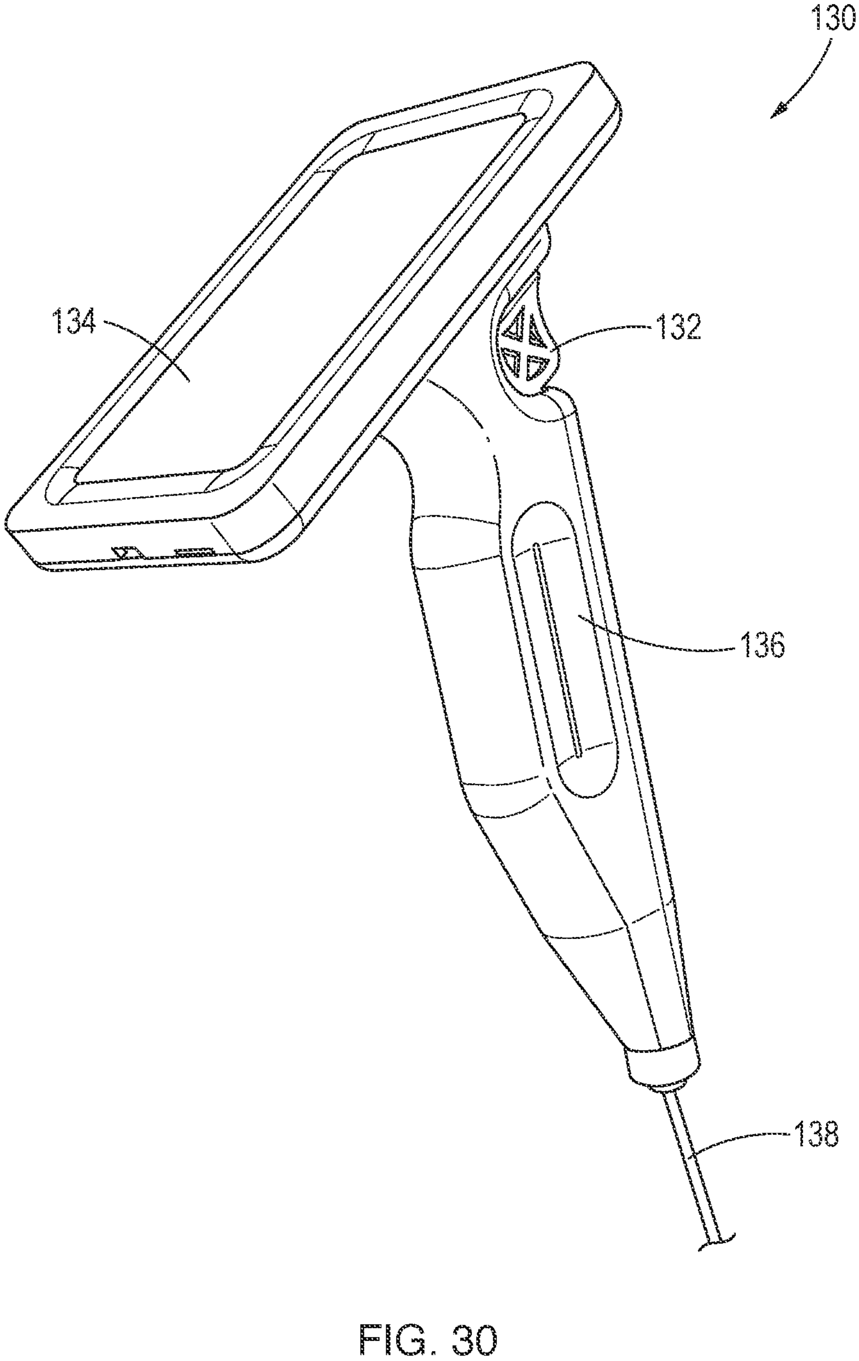
FIG. 30 is a perspective view of a controller unit.

Referring to FIG. 30, a controller 130 may be comprised of various structures and configurations. A controller 130 may include a haft 136, or stock 136, which haft 136 serves as a handle for the controller 130. A controller 130 may include a trigger 132, which trigger 132 may serve to operate and/or engage various functions with respect to the system 10. For example, and not by way of limitation, a trigger 132 could be configured to control the operation and speed of the wheels 112. Depressing the trigger 132 could simply turn on and off the hub motor 100 and the connected wheels 112. Depressing the trigger 132 further could control the speed of rotation of the hub motor 100 and wheels 112. A controller 130 may include a touch-screen 134, or screen 134 or display 134. A touch-screen 134 could be formatted and configured to control and/or set virtually any and all functions associated with the system 10. For example, and not by way of limitation, a touch-screen 134 could set the speed of rotation for the hub motor 100 and wheels. A touch-screen 134 could set the amount of air pressurized in the cavity of the core 50. A touch-screen 134 could be set to vary the speed of rotation and/or the pressurization within the cavity over time of massage. A controller 130 may include a controller cord 138, or string 138, which controller cord 138 may serve as means for sending and receiving inputs from the controller 130 to the core 50 and/or system 10. The controller 130 may be configured and formatted to monitor, display and control virtually all the functions of the system 10.

In one embodiment, a controller 130 may be operated by a user in a manner that allows the user to select a program and initiate that program by activating the trigger 132. The user may be required to pull the trigger to activate the program and produce rotation of the wheeled sprocket. Letting go of the trigger 132, or dropping the controller 130, may result in a full stop of the wheeled sprocket, which may be considered another safety feature. In one embodiment, the controller 130 may comprise a digital display and PCB controller, which may also include a variety technologies, i.e., blue tooth, one or more cameras, one or more forward-looking infrared cameras, one or more speakers, a microphone, one or more sensors, one or more terminal connectors, ports, a handle, a trigger system, or the like. The trigger 132 may be configured to allow for 0-100% speed range, or pre-programmed speed range dependent on the level the trigger is depressed. The digital display and controller PCB may show all the program options, i.e., free mode, shiatzu, facia blast, forward, reverse, oscillating, infrared, or the like. A controller 130 may also be configured to show training videos, graphics, animations, warnings, disclaimers, timing, levels, history, and/or the like. Such features may also be available to individual user accounts.

A controller 130 may be configured to be a "virtual therapist," guiding a user thru an individual massage therapy session. A controller 130 may also include diagnostic sensor technology that allows the monitoring of heart rate, blood oxygen, blood pressure, blood sugar, inflation factors, or the like. A controller 130 may be configured like a "tablet," and may control the system 10 directly, via a controller cord 138, or may control the system 10 indirectly, via a WiFi or blue tooth connection.

A method for use of the system 10 may comprise providing a rail 20, wherein the rail comprises a power reel 34 at one end of the rail and a weight reel 44 at the opposing end of the rail, and the rail 20 is mounted to a wall, and providing a core 50, wherein the core 50 comprises a carrier 52, a vessel 70, a dome 82, and a bezel 90 and the bezel 90 and the vessel 70 are removably connected with the dome 82 between the vessel 70 and the bezel 90 in a manner that creates a cavity, and the carrier 52 and the vessel 70 are operably and rotatably connected, and wherein a hub motor 100 with a wheeled sprocket is operably connected and contained within the cavity, and the carrier 52 is operably connected to the rail 20 in a manner that allows the carrier 52 and the core 50 to move along the rail 20, and providing a controller 130 that controls the functions of the hub motor 100 and wheeled sprocket, and positioning the core 50 along the rail 20, and positioning, by a user, a soft tissue of the user adjacent the dome 82 of the core 50, and rotating the wheeled sprocket, and massaging of the user's soft tissue by the wheeled sprocket thru the dome. This system of wheeled sprocket and flexible dome may provide a peristaltic wave action to the musculature of a user.

The method may further comprise providing a pump 116 and a valve 118 within the cavity of the core 50, and pressurizing the cavity, wherein the pressurization is controlled by the controller. The method may further comprise the stopping of the rotation of the wheeled sprocket if the pressurization of the cavity falls to zero, or to any pressure below 0.2 psi. The method may further comprise providing a lighting array 92 operably connected to the bezel 90 and the lighting array 92 includes infrared light sources 96. The method may further comprise the ability to rotate the wheeled sprocket in a forward direction and in a reverse direction. The method may further comprise the ability to interchange the wheeled sprocket with a different wheeled sprocket, wherein the different wheeled sprocket has a separate and distinct configuration of wheels as compared to the original wheeled sprocket.

In operation, the hub motor 100, or geared hub 100, may provide any desired combination of torque and RPM. For example, and not by way of limitation, certain embodiments may provide approximately 0-300 rpm. Certain embodiments may provide approximately 0-600 rpm, depending on gearing and transmission issues. The hub motor 100 may be described as a high torque geared hub unit that has stability in rotation throughout its speed range and relatively lower RPM. Without a geared down feature in the hub motor 100, or a geared down transmission, the hub motor 100 would typically produce a RPM that is too high and would produce little torque at low speed (less amperage), and would be unstable in its rotation against a force, or too high a speed to be safe and therapeutic. A user may be able to control the speed of wheels 112, and choose from a variety of programs, i.e., slow-fast-slow, forward-reverse-forward, or the like.

A core 50, or hub motor 100, may be configured to provide three speed ranges. A low speed may have high torque and be very stable due to the geared down hub, which low speed may be best for heavy scraping or deep milling or kneading of muscle tissue. A low speed range may be described as including speeds of approximately five (5) rpm to approximately forty (40) rpm. The low speed may allow a user to deeply penetrate damaged muscle tissue, ligaments and tendons, and/or break up scar tissue. A medium speed range may be best for facia, the layer of fat and connective tissue and skin between the muscle and top layer of skin. A medium speed range may be described as including speeds of approximately fifty (50) rpm to approximately one hundred and twenty (120) rpm. The medium speed may be used to break down or process facia, making it smooth. When facia is tight, the connective tissues pull at the subcutaneous fat layer, making it look bumpy. The medium speed may break up this connective tissue in the facia, similar to the way it works on muscles, pulling blood and tissues in linear orientation thru and along the facia. This may result in the facia restructuring, loosening the facia, which is healthier facia. The looser, even facia does not pull unevenly on the fat layer, so it appears smooth and sculpted. This may be described as facia blasting or cellulite therapy. A high speed may be best for massage. A high speed range may be described as including speeds of approximately one hundred and fifty (150) rpm to approximately three hundred (300) rpm. The high speed may send high frequency pressure waves of compression throughout all layers of tissue, thereby creating a therapeutic massage. Whether high, medium or low speed, all of these therapies would be peristaltic in nature.

In one embodiment, other, additional therapy systems may be added to a core 50 to enhance, multiply and/or compliment the milling action and massage therapy, i.e., ultra-sonic, vibration, subsonic, heat radiation, electronic stimulation, or the like.

In one embodiment, a hub motor 100 could be outside the wheel, attached to a transmission gear box that is attached to a wheeled sprocket. A hub motor 100 and planetary geared down transmission may be housed inside the hub itself, with the wheeled sprocket connected to the hub motor. The hub motor and wheeled sprocket may be mounted to the housing or vessel 70, which also holds the electronics consisting of the PCB, air pump 116, and electronic valve 118, in addition to a manual Schrader valve and pressure release valve.

In one embodiment, the hub motor and wheeled sprocket may protrude from the housing 70, or vessel 70 and be mounted to the housing 70. The hub motor 100 and wheeled sprocket may be completely covered by a dome 82, or bubble 82.

The system 10 may provide benefits that enable healing muscles, joints, tendons, ligaments, facia, and/or skin. The human body's musculature benefits from increased blood flow to promote healing. The system 10 described herein may provide a peristaltic pump action (positive displacement principle, also known as peristaltic wave or pump) where each roller wheel 112 pushes blood thru the muscle and tissue in a linear motion. This is very different from a reciprocating type massage device, or Thera Gun, which is popular but simply punches the muscle or tissue. This is also different from a massage device that simply vibrates the muscle and tissue. As the wheels 112 rotate against the body part or area, they provide the therapeutic kneading or milling action in a linear fashion, pulling and pushing blood and other tissues thru and along the axis of the muscle tissue.

However, other angles may also be beneficial, including perpendicular milling action. The system 10 may be very effective when deployed in this cross-verse orientation to break down scar and muscle tissue. Muscles that have been previously damaged, perhaps multiple times, may be full of scar tissue from an injury or tear and are past the repair phase and moved into the restructuring phase. In such a situation, intense massage therapy may be required to go back to the repair phase, and then to the restructuring phase. This type of intense massage therapy may be labor intensive, making the current system 10 more suited to accomplish such massage therapy because it requires less effort while maintaining great effectiveness.

Regardless of whether the therapy is for a new injury or an old injury, external massage, manipulation and scraping may be extremely difficult and labor intensive for a therapist as this is usually done by bare hands. This may be especially true in deep areas with thick, heavy muscle tissue like the back, glutes hamstrings, groin, quadriceps, calves, shoulders, etc. The system 10 described herein works in a manner similar to a therapist by stroking the affected muscle from end to end in various patterns and techniques. The system 10 may also affect surrounding and connected muscles and joints. The system 10 may improve the body's healing ability using its milling and scraping massage therapy to promote more intense microphage, fibroblast, satellite/myoblast, and connective tissue activation. It may also promote the development of blood vessels and nerves during the repair phase. During the remolding phase, however, massage, manipulation and scraping may be extremely valuable in augmenting and facilitating the orientation of newly forming connective and scar tissues in line with the relevant muscle.

Generally, the core 50, and more precisely the wheeled sprocket, massages, manipulates or scrapes the muscles, tendons, facia and connective tissue in an acute, linear, stable, and ultra-sustained fashion. Thus providing more intensity, volume, depth, breadth, and repeatability than a therapist using hands, a scraping blade, or a massage gun. The system 10 may also be used to realign joints, ligaments, muscles and tendons by its creation and application of pressure waves at all speeds, which may allow the body to release an unnatural joint position or joint impingement, in spine, hips, or shoulders. The system 10 may also be utilized for massage therapy of the feet, hands, upper neck and whole of the spine by use of high intensity pressure waves that help increase blood flow to the extremities and provide realignment and activation of joints.

The present invention may be embodied in other specific forms without departing from its fundamental functions or essential characteristics. The described embodiments are to be considered in all respects only as illustrative, and not restrictive. All changes which come within the meaning and range of equivalency of the illustrative embodiments are to be embraced within their scope.

What is claimed and desired to be secured by United States Letters Patent is:

1. A peristaltic massage therapy apparatus, comprising:
- a vessel;
- a hub motor operably connected to and within the vessel, wherein the hub motor further comprises a sprocket and a plurality of wheels and the sprocket is operably and rotatably connected to the hub motor and the plurality of wheels is operably and rotatably connected to the sprocket, and the hub motor can rotate the sprocket in a manner that enables the plurality of wheels to produce a peristaltic wave in a user's soft tissues;
- a dome connected to the vessel in a manner that encloses the hub motor, sprocket, and plurality of wheels within a cavity formed by the vessel and the dome;
- a bezel removably connected to the vessel, with the dome between the bezel and the vessel, in a manner that seals the cavity; and
- a controller for controlling the functions of the hub motor.

2. The massage therapy apparatus of claim 1, further comprising:
- a rail mounted to a wall; and
- a carrier, wherein the vessel is operably, rotatably connected to the carrier and the carrier is operably connected to the rail in a manner that allows the carrier and vessel to move along the rail.

3. The massage therapy apparatus of claim 2, wherein the rail further comprises a power reel at one end of the rail and a weight reel at the opposing end of the rail.

4. The massage therapy apparatus of claim 3, wherein the carrier and the vessel are removably positionable along the rail.

5. The massage therapy apparatus of claim 1, further comprising:
- a pump and a valve both operably disposed within the vessel in a manner that enables pressurization of the cavity, and the pressurization is controllable by the controller.

6. The massage therapy apparatus of claim 5, wherein the controller comprises a touch-screen, and the controller provides a selection of massage therapy programs.

7. The massage therapy apparatus of claim 1, further comprising:
- a lighting array operably connected to the bezel, wherein the lighting array comprises a light source, a heat sink surrounding the light source, and a lens covering the light source.

8. The massage therapy apparatus of claim 7, wherein the lighting array comprises multiple light sources and each light source is an LED-infrared light source.

9. The massage therapy apparatus of claim 1, wherein the plurality of wheels comprises primary wheels and secondary wheels, and the primary wheels are operably and rotatably connected to the sprocket and the secondary wheels operably and rotatably connected to the sprocket and on both sides of the primary wheels.

10. An apparatus for providing massage therapy to soft tissues, comprising:
- a vessel, wherein the vessel is formed to contain a hub motor;
- the hub motor operably connected to and within the vessel, wherein the hub motor further comprises a sprocket and a plurality of wheels and the sprocket is operably and rotatably connected to the hub motor and the plurality of wheels is operably and rotatably connected to the sprocket, and the hub motor can rotate the sprocket in both a forward direction and a backward direction;
a dome connected to the vessel in a manner that encloses the hub motor, sprocket, and plurality of wheels within a cavity formed by the vessel and the dome;
a bezel removably connected to the vessel, with the dome between the bezel and the vessel, in a manner that seals the cavity;
a pump and a valve both operably disposed within the vessel in a manner that enables pressurization of the cavity; and
a controller for controlling the functions of the hub motor and the pressurization of the cavity.

11. The apparatus of claim 10, further comprising:
a rail mounted to a wall, wherein the rail further comprises a power reel and a weight reel at one end of the rail; and
a carrier, wherein the vessel is operably, rotatably connected to the carrier and the carrier is operably connected to the rail in a manner that allows the carrier and vessel to move along the rail and be removably positioned at regular intervals along the rail.

12. The apparatus of claim 11, further comprising:
a lighting array operably connected to the bezel, wherein the lighting array comprises a plurality of light sources, a heat sink surrounding each light source, and a lens covering each light source.

13. The apparatus of claim 12, wherein the plurality of light sources is each an LED-infrared light source.

14. The apparatus of claim 13, wherein the controller comprises a touch-screen, and the controller provides a selection of massage therapy programs.

15. A method for providing physical therapy, comprising:
providing a rail, wherein the rail comprises a power reel and a weight reel, and the rail is mounted to a wall;
providing a core, wherein the core comprises a carrier, a vessel, a dome, and a bezel and the bezel and the vessel are removably connected with the dome between the vessel and the bezel in a manner that creates a cavity, and the carrier and the vessel are operably and rotatably connected, and wherein a hub motor with a wheeled sprocket is operably connected and contained within the cavity, and the carrier is operably connected to the rail in a manner that allows the carrier and the core to move along the rail;
providing a controller that controls the functions of the hub motor and wheeled sprocket;
positioning the core along the rail;
positioning, by a user, a soft tissue of the user adjacent the dome of the core;
rotating the wheeled sprocket; and
producing a peristaltic wave in the user's soft tissue by the wheeled sprocket thru the dome.

16. The method of claim 15, further comprising:
providing a pump and a valve within the cavity of the core;
pressurizing the cavity, after positioning the core along the rail, wherein the pressurization is controlled and monitored by the controller.

17. The method of claim 16, further comprising:
stopping the rotation of the wheeled sprocket if the pressurization of the cavity falls below 0.2 psi.

18. The method of claim 16, further comprising:
providing a lighting array operably connected to the bezel; and
providing, by the lighting array, infrared light to the user's soft tissue.

19. The method of claim 16, wherein the producing a peristaltic wave in the user's soft tissue further comprises rotating the wheeled sprocket in a forward direction and rotating the wheeled sprocket in a reverse direction.

20. The method of claim 15, wherein the wheeled sprocket is interchangeable with a different wheeled sprocket.

* * * * *